(12) United States Patent
Schwarz

(10) Patent No.: US 8,980,298 B2
(45) Date of Patent: Mar. 17, 2015

(54) IMPLANTABLE TIZANIDINE COMPOSITIONS AND METHODS OF TREATMENT THEREOF

(71) Applicant: Endo Pharmaceuticals Solutions Inc., Chadds Ford, PA (US)

(72) Inventor: Alexander Schwarz, Brookline, MA (US)

(73) Assignee: Braeburn Pharmaceuticals BVBA SPRL, Brussels (BE)

( * ) Notice: Subject to any disclaimer, the term of this patent is extended or adjusted under 35 U.S.C. 154(b) by 0 days.

(21) Appl. No.: 13/659,420

(22) Filed: Oct. 24, 2012

(65) Prior Publication Data

US 2013/0108680 A1  May 2, 2013

Related U.S. Application Data

(60) Provisional application No. 61/550,653, filed on Oct. 24, 2011.

(51) Int. Cl.
| | | |
|---|---|---|
| *A61K 9/00* | (2006.01) | |
| *A61K 31/433* | (2006.01) | |
| *A61K 9/20* | (2006.01) | |
| *A61K 45/06* | (2006.01) | |

(52) U.S. Cl.
CPC ............ *A61K 9/0002* (2013.01); *A61K 31/433* (2013.01); *A61K 9/0024* (2013.01); *A61K 9/0092* (2013.01); *A61K 9/2013* (2013.01); *A61K 9/2054* (2013.01); *A61K 45/06* (2013.01)
USPC ......................................... 424/424; 514/362

(58) Field of Classification Search
None
See application file for complete search history.

(56) References Cited

U.S. PATENT DOCUMENTS

| | | | | |
|---|---|---|---|---|
| 3,843,668 | A * | 10/1974 | Neumann ..................... | 548/126 |
| 5,035,891 | A | 7/1991 | Runkel | |
| 5,798,114 | A * | 8/1998 | Elsberry et al. .............. | 424/423 |
| 7,214,206 | B2 | 5/2007 | Rue | |
| 7,452,868 | B2 | 11/2008 | Kuzma | |
| 7,510,549 | B2 | 3/2009 | Rue | |
| 7,842,303 | B2 | 11/2010 | Kuo | |
| 7,850,639 | B2 | 12/2010 | Rue | |
| 7,858,110 | B2 | 12/2010 | Kuzma | |
| 7,960,335 | B2 | 6/2011 | Kuzma | |
| 8,071,537 | B2 | 12/2011 | Kuzma | |
| 2005/0118256 | A1 | 6/2005 | Sen et al. | |
| 2008/0194655 | A1 * | 8/2008 | Bull et al. ..................... | 514/362 |
| 2009/0098182 | A1 | 4/2009 | Kuzma | |
| 2009/0208540 | A1 * | 8/2009 | Kuzma et al. ................. | 424/400 |
| 2010/0080835 | A1 | 4/2010 | Kuzma | |
| 2011/0059140 | A1 * | 3/2011 | Winter et al. ................. | 424/400 |
| 2011/0236456 | A1 | 9/2011 | Kuzma | |
| 2011/0244015 | A1 | 10/2011 | Kuzma | |
| 2011/0275980 | A1 * | 11/2011 | Weber et al. .................... | 604/20 |

FOREIGN PATENT DOCUMENTS

| | | |
|---|---|---|
| WO | WO-2009060473 A2 | 5/2009 |
| WO | WO-2009129432 A1 | 10/2009 |
| WO | WO-2009129460 A2 | 10/2009 |
| WO | WO-2010039643 A1 | 4/2010 |
| WO | WO-2010039717 A1 | 4/2010 |
| WO | WO-2010039722 A1 | 4/2010 |
| WO | WO-2011116132 A1 | 9/2011 |

OTHER PUBLICATIONS

Non-Final Office Action dated Oct. 25, 2013 for U.S. Appl. No. 13/899,704.
International Application Serial No. PCT/US2012/061701, International Search Report mailed Feb. 12, 2013, 7 pgs.
International Application Serial No. PCT/US2012/061701, International Partial Search Report mailed Dec. 5, 2012, 7 pgs.
"The VANTAS Insertion and Removal Guide", Instructional Pamphlet, 9 pgs, Jun. 30, 2014.
Chien, Yie W., "Novel Drug Delivery Systems", Informa Healthcare, 2nd Edition, vol. 50, Chapter 2, 7 pgs, Dec. 31, 2009.
Notification Concerning Transmittal of International Preliminary Report on Patentability and Written Opinion of The International Searching Authority received in International Application No. PCT/US2012/061640 Issued on Apr. 29, 2014.
Notification Concerning Transmittal of International Preliminary Report on Patentability and Written Opinion of The International Searching Authority received in International Application No. PCT/US2012/061701 Issued on Apr. 29, 2014.
Notification Concerning Transmittal of International Preliminary Report on Patentability and Written Opinion of The International Searching Authority received in International Application No. PCT/US2012/061644 Issued on Apr. 29, 2014.
Final Office Action Issued by the U.S. Patent and Trademark Office for U.S. Appl. No. 13/899,704 Dated Apr. 16, 2014.
International Application Serial No. PCT/US2012/061644, International Search Report mailed Nov. 29, 2012.
International Application Serial No. PCT/US2012/061640, International Search Report mailed Nov. 29, 2012.

* cited by examiner

*Primary Examiner* — Frederick Krass
*Assistant Examiner* — Celeste A Roney
(74) *Attorney, Agent, or Firm* — RatnerPrestia

(57) ABSTRACT

A method of treating the symptoms of spasticity comprises implanting a reservoir-based drug delivery composition into a subject to systemically deliver a therapeutically effective amount of tizanidine to the subject for a long period of time (e.g., one month or one year). The drug delivery composition may include a rate-controlling excipient (e.g., an elastomeric polymer) defining a reservoir containing at least one discrete solid dosage form (e.g., one or more pellets), which includes tizanidine free base and optionally, a sorption enhancer.

14 Claims, 18 Drawing Sheets

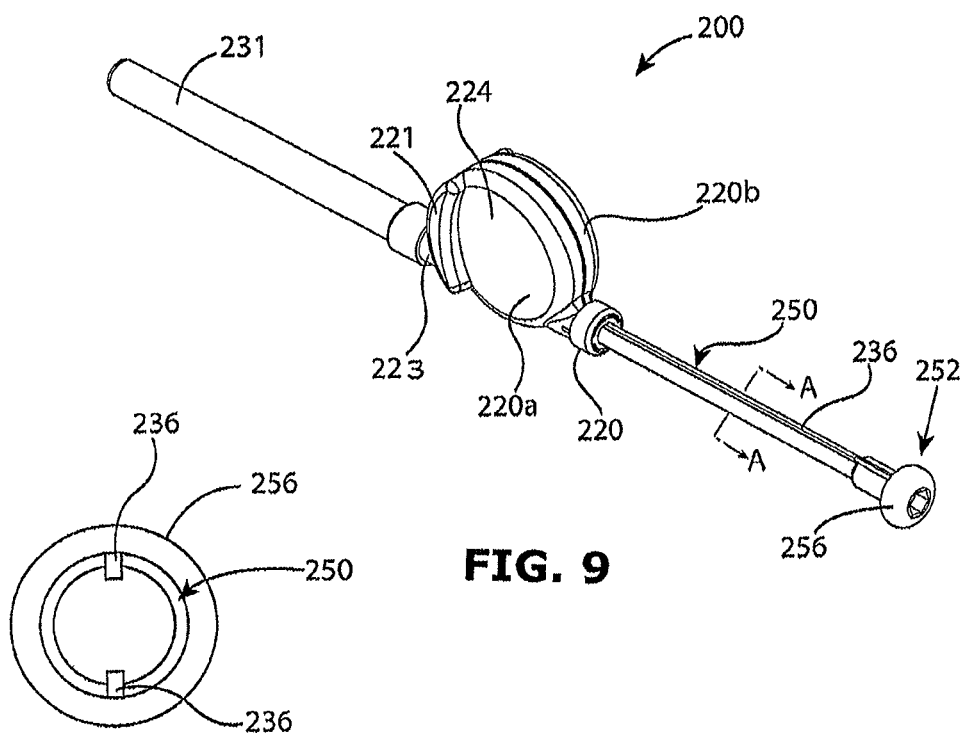
FIG. 9
FIG. 9A
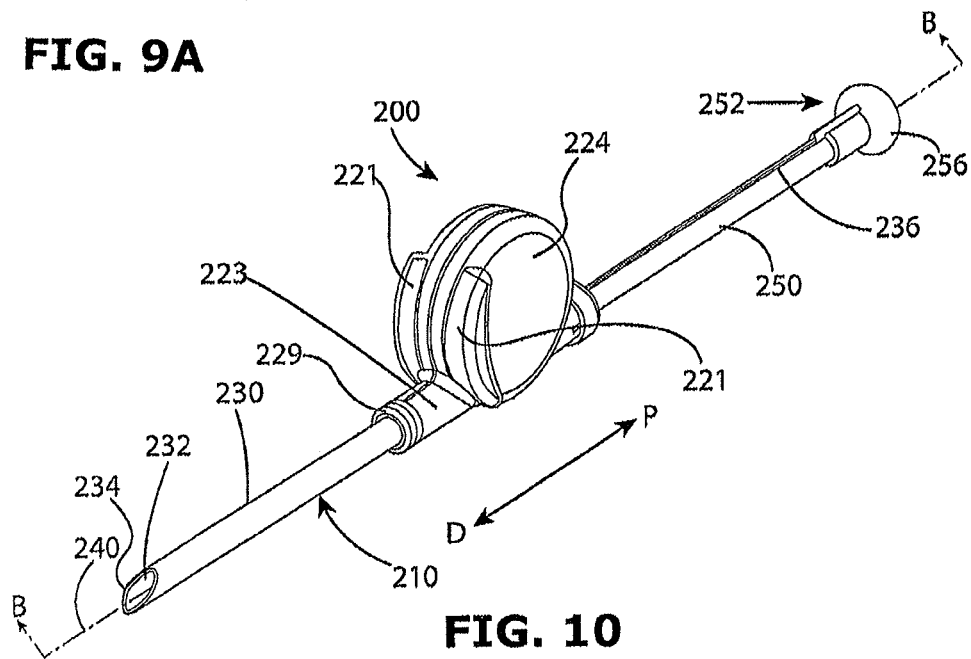
FIG. 10

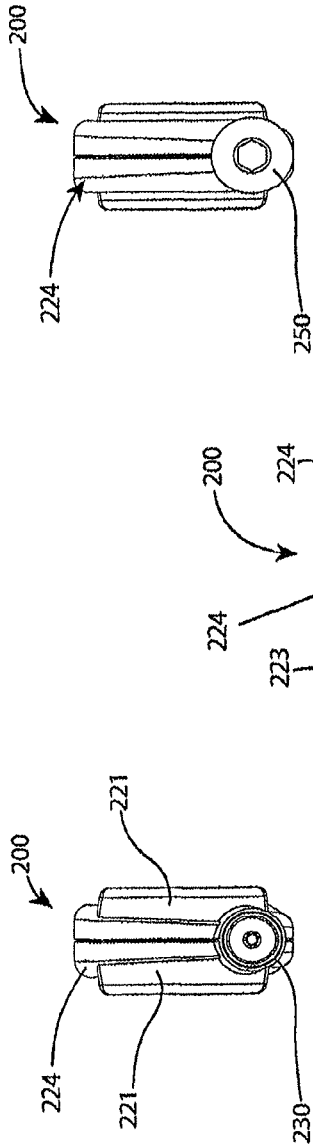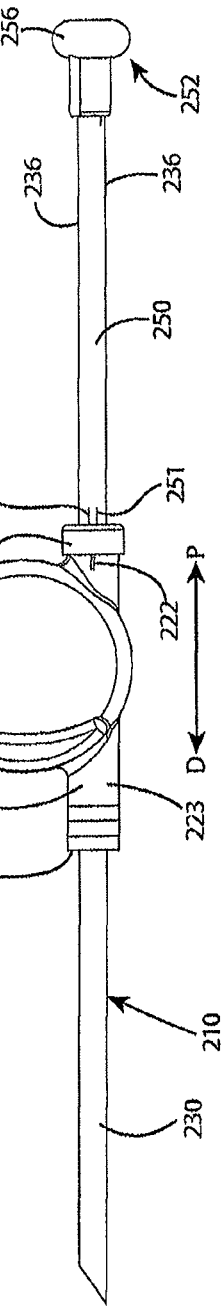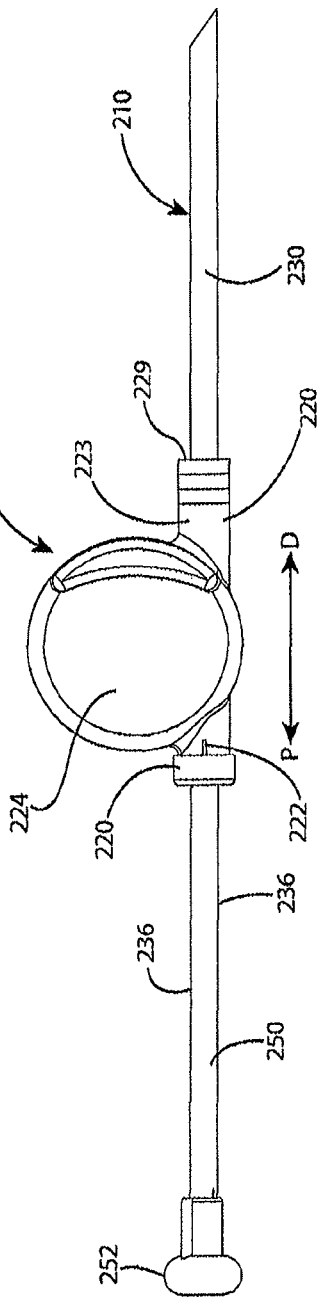

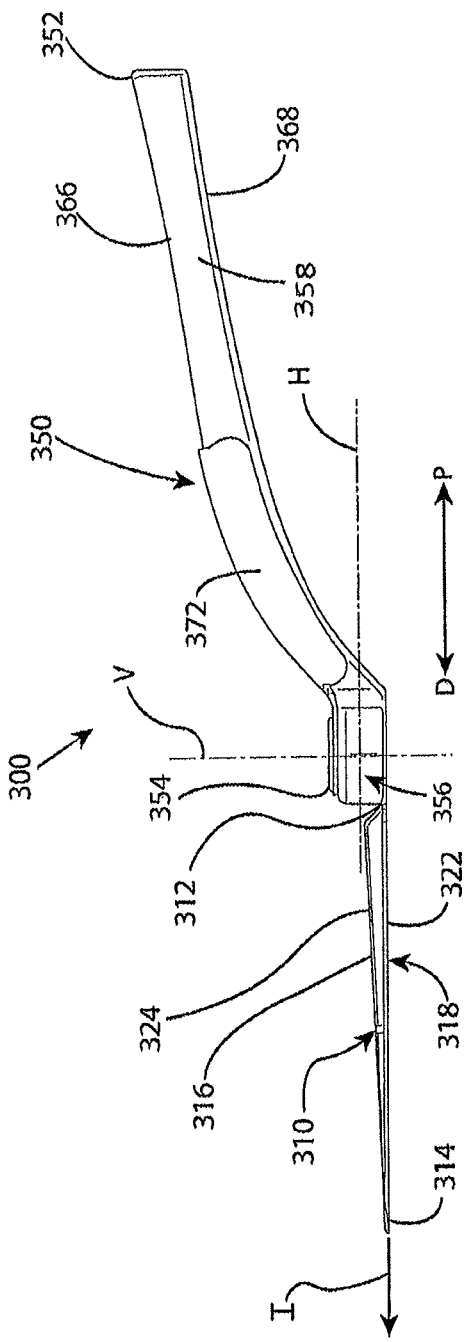
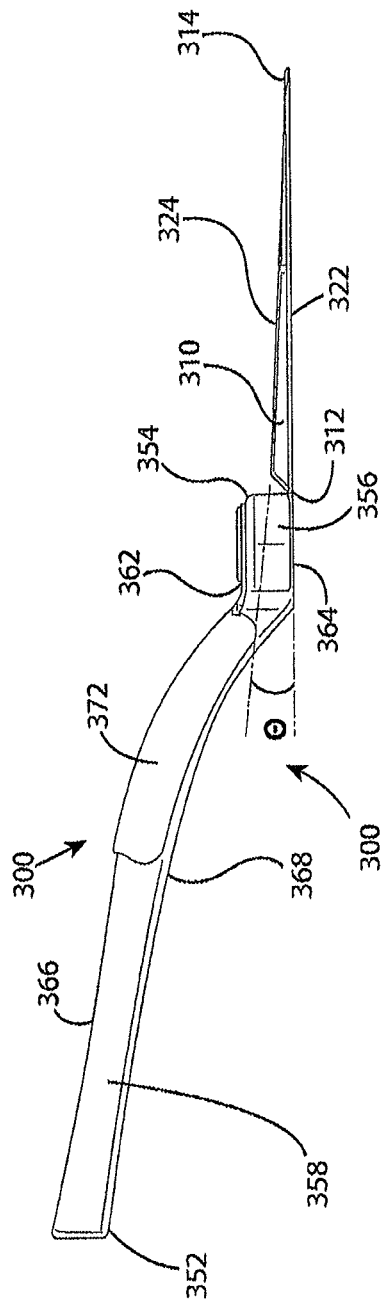
FIG. 19
FIG. 20

US 8,980,298 B2

IMPLANTABLE TIZANIDINE COMPOSITIONS AND METHODS OF TREATMENT THEREOF

CROSS-REFERENCE TO RELATED APPLICATIONS

This application claims priority to U.S. Application No. 61/550,653, filed Oct. 24, 2011, which is incorporated by reference herein, in its entirety and for all purposes.

FIELD OF THE INVENTION

The invention relates to reservoir-based drug delivery compositions that are implantable into a subject in order to deliver therapeutically effective amounts of tizanidine at a pseudo-zero order rate, for extended periods of time (e.g., at least one month, one year, etc.).

BACKGROUND OF THE INVENTION

Drug compositions come in many different forms and may be administered to a patient via several different routes, such as oral, parenteral, topical, intravenous, subcutaneous, intranasal, etc. Depending on the active and the treatment desired, different routes of administration may be preferable.

Some diseases and conditions may be long lasting, requiring treatment for many weeks, months, or even years. Typically, a patient taking a traditional oral dosage form (e.g., tablets or capsules) may be required to take the oral dose at least once per day for the duration of the treatment. For example, a patient may need to take an oral dose twice a day for a year or longer. The problem with treatments that require continuous dosage over a long period of time is that often the patient may not be compliant in taking the medications. In other words, the patient may forget, believe the treatment is unnecessary, or grow tired of having to take many pills over an extremely long period of time. Accordingly, treatments are necessary which can alleviate these compliance issues, but still provide effective and efficient treatment to the patient.

Tizanidine is an imidazoline central $\alpha_2$-adrenoceptor agonist that is effective at managing spasticity, which is an involuntary tension, stiffening or contraction of muscles. Spasticity is typically associated with conditions such as multiple sclerosis (MS), cerebral palsy, stroke, or brain or spinal cord injury. It is estimated that spasticity affects 500,000 people in the United States and 12 million people worldwide. Tizanidine is in a class of medications called skeletal muscle relaxants, and works by slowing action in the brain and nervous system to allow muscles to relax. Treatment of spasticity typically lasts many years. Many of the oral dosage forms of tizanidine that are currently on the market (e.g., Zanaflex®) are short-acting. Because of the short duration of effect, a patient must take a pill or capsule several times per day if relief from spasticity is needed throughout the day.

Currently, the only treatments for spasticity which do not involve oral dosage forms are localized botox injections, or an implantable drug pump which delivers drug intrathecally. Each of these treatments involve significant risk to the patient, and do not provide long-term relief. For example, botox injections can produce side effects such as headache, bruising, flu-like symptoms, nausea, and temporary pain and redness at the injection site. Moreover, the long term effects of multiple botox injections are not known. Implanting a drug pump involves major surgery to insert the large (e.g., hockey puck sized) pump and reservoir along with its catheter, which is connected to the spinal cord so that drug can be pumped into the spinal fluid. In addition to the risks of major surgery involving the spinal cord, the pump needs to be refilled frequently.

Accordingly, there has remained a need for effective dosage forms that provide therapeutically effective amounts of drugs that treat spasticity at relatively constant rates over a long period of time.

SUMMARY OF THE INVENTION

Aspects of the present invention include reservoir-based drug delivery compositions, which may be implanted into a subject in order to deliver a therapeutically effective amount of tizanidine to the subject for long periods of time (e.g., at least one month, at least six months, at least one year, at least 18 months, at least two years, at least 30 months, etc.). The therapeutically effective amount of tizanidine may be delivered at a pseudo-zero order rate (e.g., zero order rate). Accordingly, the present invention is directed to tizanidine compositions, methods of treatment (e.g., treating spasticity), methods of delivering tizanidine, subcutaneous delivery systems, and kits regarding the same.

According to an embodiment of the present invention, a drug delivery composition comprises a drug elution rate-controlling excipient comprising an elastomeric polymer defining a reservoir, and the reservoir contains at least one discrete solid dosage form comprising tizanidine free base. The drug delivery composition is in an implantable dosage form. According to one aspect of the present invention, the at least one discrete solid dosage form comprises 75-97 wt % (e.g., about 88 wt %) tizanidine free base based on the total weight of the at least one discrete solid dosage form and 1-25 wt % (e.g., about 10 wt %) of at least one sorption enhancer based on the total weight of the at least one discrete solid dosage form.

According to another embodiment of the present invention, a method of treating spasticity comprises implanting a reservoir-based drug delivery composition into a subject to systemically deliver a therapeutically effective amount of tizanidine to the subject for a period of time of at least one month. The drug delivery composition may comprise at least one discrete solid dosage form comprising tizanidine free base surrounded by an excipient comprising at least one polymer. The therapeutically effective amount of the tizanidine may be delivered at a pseudo-zero order rate (e.g., zero order rate). The at least one discrete solid dosage form may comprise 75-97 wt % (e.g., about 88 wt %) tizanidine free base based on the total weight of the at least one discrete solid dosage form and 1-25 wt % (e.g., about 10 wt %) of at least one sorption enhancer based on the total weight of the at least one discrete solid dosage form.

According to another embodiment of the present invention, a method of systemically delivering tizanidine to a subject includes releasing a therapeutically effective amount of tizanidine from a reservoir-based composition comprising a polymeric rate-controlling excipient defining a reservoir containing at least one discrete solid dosage form comprising tizanidine free base to provide a pseudo-zero order elution rate (e.g., zero order rate) to the subject for a period of time of at least one month.

According to another embodiment of the present invention, a drug delivery composition comprises a drug elution rate-controlling excipient comprising an elastomeric polymer defining a reservoir, and the reservoir contains at least one discrete solid dosage form comprising tizanidine free base.

According to another embodiment of the present invention, a subcutaneous delivery system comprises an elastomeric reservoir implant comprising at least one discrete solid dosage form surrounded by a polymeric rate-controlling excipient. The at least one discrete solid dosage form comprises tizanidine free base. The subcutaneous delivery system provides for release of the tizanidine at an elution rate suitable to provide a therapeutically effective amount of the tizanidine to a subject at a pseudo-zero order rate for a period of time of at least one month.

According to another embodiment of the present invention, a kit for subcutaneously placing a drug delivery composition comprises a reservoir-based drug delivery composition comprising a polymeric rate-controlling excipient defining a reservoir containing at least one discrete solid dosage form comprising tizanidine free base; and an implanter for inserting the reservoir-based drug delivery composition beneath the skin, and optionally instructions for performing the implantation and explantation of the drug delivery composition.

According to another embodiment of the present invention, a method of delivering a therapeutically effective amount of tizanidine from an implantable drug delivery composition comprises implanting a reservoir-based drug delivery composition into a subject to systemically deliver a therapeutically effective amount of tizanidine to the subject at a pseudo-zero order rate for a period of time of at least one month. The drug delivery composition comprises at least one discrete solid dosage form surrounded by an excipient comprising at least one polymer, and the at least one discrete solid dosage form comprises tizanidine free base. The polymer comprises a substantially non-porous, elastomeric polymer comprising soft and hard segments, and the relative content of the soft and hard segments provide an elution rate within a target range of average daily elution rate for the tizanidine.

According to another embodiment of the present invention, a drug delivery composition includes a rate-controlling excipient defining a reservoir which contains at least one discrete solid dosage form comprising tizanidine free base. The rate-controlling excipient comprises a substantially non-porous, elastomeric polymer comprising soft and hard segments selected based on the relative content of soft and hard segments of the polymer to obtain an elution rate within a target range of average daily elution rate for the tizanidine. The at least one discrete solid dosage form comprises at least one sorption enhancer in an amount effective to modulate the average daily elution rate of the tizanidine to provide for release of the tizanidine at pseudo-zero order within the target range at the therapeutically effective amount for a period of time of at least one month. The amount of sorption enhancer is preferably directly proportional to the average daily elution rate. The tizanidine free base composition preferably delivers a therapeutically effective amount of tizanidine to a subject at a target range of about 100 micrograms/day to about 5,000 micrograms/day.

According to another embodiment of the present invention, a subcutaneous delivery system for releasing tizanidine at a pseudo-zero order comprises an elastomeric reservoir implant comprising a rate-controlling excipient defining a reservoir. The rate-controlling excipient comprises a substantially non-porous elastomeric polymer having a relative content of hard segments and soft segments to provide an elution rate within a target range of average daily elution rate for the tizanidine. The reservoir contains at least one discrete solid dosage form comprising tizanidine free base and an effective amount of at least one sorption enhancer to modulate the elution rate of the tizanidine for release of a therapeutically effective amount of the tizanidine within the target range at pseudo-zero order for a period of time of at least one month. The amount of sorption enhancer may be directly proportional to the average daily elution rate.

According to another embodiment of the present invention, a method of choosing an implantable drug delivery composition comprises selecting a rate-controlling excipient comprising a substantially non-porous, elastomeric polymer comprising soft and hard segments for defining a reservoir based on the relative content of soft and hard segments of the polymer to adjust the elution rate within a target range of average daily elution rate for tizanidine; and selecting and formulating tizanidine free base and at least one sorption enhancer in order to modulate the elution rate at a therapeutically effective amount of the tizanidine at pseudo-zero order for a period of time of at least one month, wherein the amount of sorption enhancer is directly proportional to the average daily elution rate.

According to another embodiment of the present invention, a method of making an implantable drug delivery composition includes: (a) selecting a substantially non-porous elastomeric polymer comprising soft and hard segments based on the relative content and molecular weights of the soft and hard segments of the polymer to provide an elution rate within a target range of average daily elution rate for tizanidine; (b) forming a hollow tube from the elastomeric polymer (see e.g., FIG. 2); (c) selecting and formulating tizanidine free base and at least one sorption enhancer in order to produce an elution rate at a therapeutically effective amount of tizanidine at pseudo-zero order for a period of time of at least one month, wherein the amount of sorption enhancer is directly proportional to the average daily elution rate; (d) loading at least one discrete solid dosage form comprising the tizanidine free base and the at least one sorption enhancer into the tube; and (e) sealing both ends of the tube to form a sealed cylindrical reservoir-based drug delivery composition.

BRIEF DESCRIPTION OF THE DRAWINGS

The invention may be further understood by reference to the drawings in which:

FIG. 9 is a perspective view of an insertion instrument used in the kit of FIG. 8;

FIG. 9A is a cross-sectional view about section line A-A in FIG. 9;

FIG. 10 is another perspective view of the insertion instrument of FIG. 8;

FIG. 11 is a distal end view of the insertion instrument of FIG. 8;

FIG. 12 is a proximal end view of the insertion instrument of FIG. 8;

FIG. 13 is a side elevation view of the insertion instrument of FIG. 8;

FIG. 14 is another side elevation view of the insertion instrument of FIG. 8;

FIG. 19 is a side elevation view of a tunneling instrument used in the kit of FIG. 18;

FIG. 20 is another side elevation view of the tunneling instrument of FIG. 18;

DETAILED DESCRIPTION OF THE INVENTION

Figure 1:
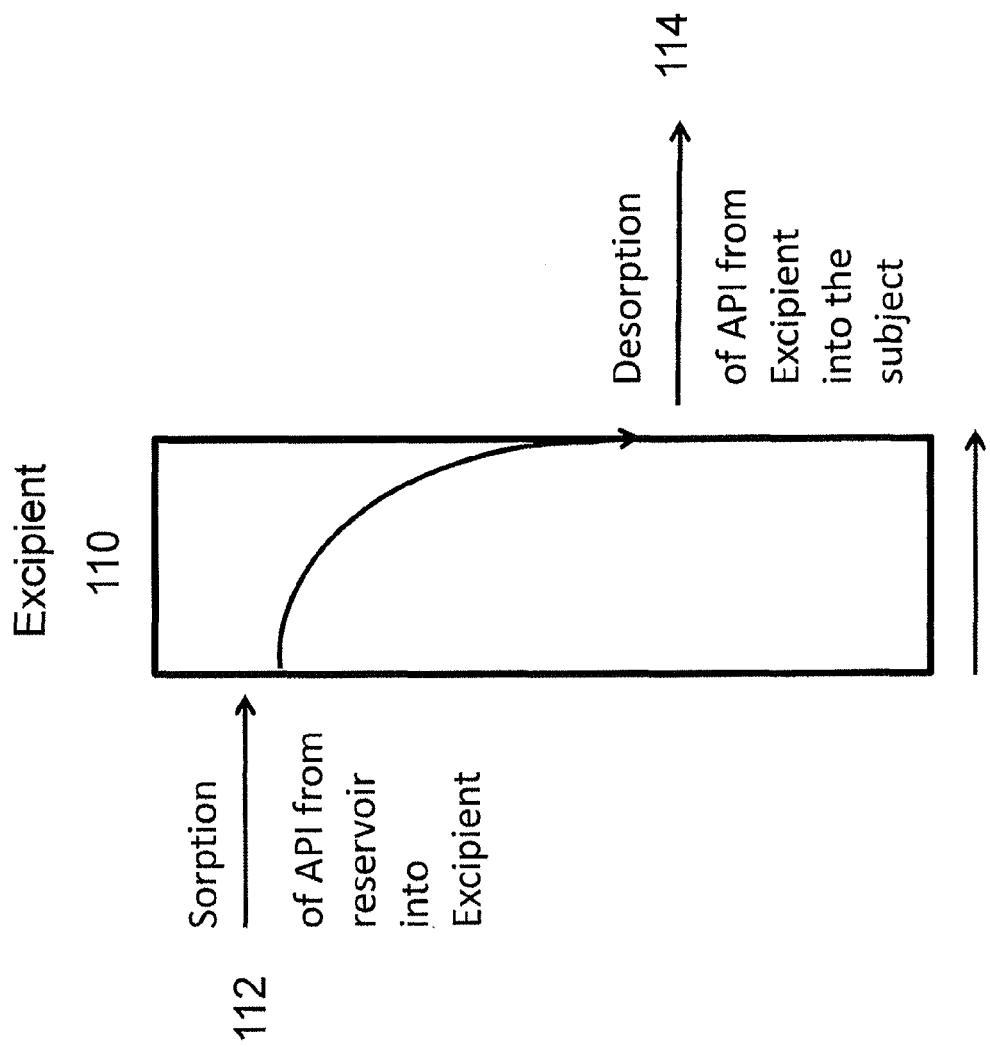
FIG. 1 depicts the role of the excipient in a reservoir-based drug delivery composition according to one aspect of the present invention.

Aspects of the present invention include methods of treatment, such as methods of treating spasticity; methods of delivering tizanidine from an implantable composition in a therapeutically effective amount to a patient; reservoir-based tizanidine delivery compositions; subcutaneous delivery systems for tizanidine; and kits for subcutaneous delivery of tizanidine.

As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest, delay the onset of or partially prevent a target disease or condition or one or more symptoms thereof.

The terms "active pharmaceutical ingredient," "API," "drug," or "active" may be used herein interchangeably to refer to the pharmaceutically active compound(s) in the drug delivery composition. This is in contrast to other ingredients in the drug delivery composition, such as excipients, which are substantially or completely pharmaceutically inert. The API in exemplary embodiments of the present invention is tizanidine free base.

The term "pharmaceutically acceptable," as used herein, means approved by a regulatory agency, e.g. of the U.S. Federal or a state government or listed in the U.S. Pharmacopeia or other generally recognized pharmacopeia for use in animals, and more particularly in humans.

The terms "subject" and "patient", are used interchangeably herein and refer to a mammalian individual, such as a human being.

Each compound used herein may be discussed interchangeably with respect to its chemical formula, chemical name, abbreviation, etc. For example, PTMO may be used interchangeably with poly(tetramethylene oxide). Additionally, each polymer described herein, unless designated otherwise, includes homopolymers, copolymers, terpolymers, and the like.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of." Unless specified otherwise, all values provided herein include up to and including the endpoints given, and the values of the constituents or components of the compositions are expressed in weight percent of each ingredient in the composition.

Treatment of Spasticity

Spasticity is an involuntary tension, stiffening or contractions of muscles, which typically results from an injury to a part of the central nervous system (e.g., brain or spinal cord) that controls voluntary movements and results in increased activity or excitability in muscles. Spasticity is most often related to cerebral palsy, multiple sclerosis (MS), physical trauma (e.g., a brain or spinal cord injury), a blockage or bleeding in the brain (e.g., a stroke), or an infection (e.g., meningitis or encephalitis). Symptoms of spasticity, e.g., the involuntary tension, stiffening or contractions of muscles, may range from slight muscle stiffness to permanent shortening of the muscle (contracture). Additional symptoms of spasticity may include, but are not limited to, increased muscle tone, overactive reflexes, involuntary movements that may include spasms (brisk and/or sustained involuntary muscle contractions) or clonus (a series of fast involuntary contractions), pain, decreased functional abilities and delayed motor development, abnormal posture, and contractures (permanent contractions of the muscle and tendon due to severe persistent stiffness and spasms). Spasticity may be constantly present or event-triggered, and may result in pain that impacts daily life activities.

Tizanidine is an imidazoline central $\alpha_2$-adrenoceptor agonist that is effective at managing spasticity. Tizanidine is in a class of medications called skeletal muscle relaxants, and works by slowing action in the brain and nervous system to allow muscles to relax. Treatment of spasticity, particularly when associated with conditions or injuries such as MS, stroke, or brain or spinal cord injury, typically lasts many months or years. Many of the oral dosage forms of tizanidine that are currently on the market (e.g., Zanaflex®) are short-acting; e.g., have a half-life in the blood of less than two hours. Because of the short duration of effect, a patient must take a pill or capsule several times per day if relief from spasticity is needed throughout the day. Moreover, a patient taking oral forms of tizanidine may experience one or more side effects, particularly if the oral dose is calculated to produce a relatively high plasma concentration of the drug in order to prolong its therapeutic effect. Such side effects include constipation; dizziness; drowsiness; dry mouth; flushing; tiredness; weakness; severe allergic reactions (including rash, hives, itching, difficulty breathing, tightness in the chest, and swelling of the mouth, face, lips, or tongue); neurological symptoms such as change in emotions, mood, or behavior; hallucinations; increased muscle spasms; muscle weakness; slow heartbeat; trouble urinating or lack of bladder control; urinary tract infection; and yellowing of the skin or eyes.

Treatment of one or more of the symptoms of spasticity according to embodiments of the present invention include treatment of one or more symptoms known to one of ordinary skill in the art. As discussed above, symptoms of spasticity may include, but are not limited to, involuntary tension, stiffening or contractions of muscles. The treatment of one or more of the symptoms of spasticity can require long-lasting treatment, often on the order of several months or years. The treatment of symptom(s) of spasticity in accordance with the present invention is directed to monotherapy (i.e., as a subject's only spasticity medication) or adjunctive therapy (i.e., used in addition to (with or after) treatment with one or more other spasticity medications). When the treatment is used as monotherapy, the treatment may comprise the patient's initial or "first-line" spasticity therapy.

By "treatment," it is intended that a pharmaceutically effective amount of tizanidine would be administered via the drug delivery composition, which will inhibit, or at least partially arrest or partially prevent or suppress one or more symptoms of spasticity. For example, treatment may include treatment that can suppress involuntary tension, stiffening and/or contractions of muscles. The treatment is particularly effective in that once the implant is administered to the patient, the patient will continue to receive a therapeutically effective dose for the intended duration of the implant (e.g., one month, three months, six months, one year, 18 months, two years, 30 months, or more). The patient may also experience less and/or reduced severity of side effects when tizanidine is administered via a drug delivery composition according to embodiments of the invention. This is in contrast to an oral dose, which requires compliance by the patient and continued oral administration consistently over the same duration of time, and which may produce unwanted side effects.

According to one aspect of the present invention, a method of treating one or more symptoms of spasticity comprises implanting a reservoir-based drug delivery composition into a subject to systemically deliver a therapeutically effective amount of tizanidine to the subject for a period of time of at least one month. The drug delivery composition comprises at least one discrete solid dosage form comprising tizanidine free base surrounded by an excipient comprising at least one polymer.

According to another aspect of the present invention, a method of systemically delivering tizanidine to a subject includes releasing a therapeutically effective amount of tizanidine from a reservoir-based composition comprising a polymeric rate-controlling excipient defining a reservoir containing at least one discrete solid dosage form comprising tizanidine free base to provide a pseudo-zero order elution rate (e.g., zero order rate) to the subject for a period of time of at least one month.

According to another embodiment, a drug delivery composition comprises a drug elution rate-controlling excipient comprising an elastomeric polymer defining a reservoir. The reservoir contains at least one discrete solid dosage form comprising tizanidine free base, and the drug delivery composition is in an implantable dosage form. The reservoir preferably contains at least one discrete solid dosage form comprising 75-97 wt % tizanidine free base based on the total weight of the at least one discrete solid dosage form; 1-25 wt % of at least one sorption enhancer based on the total weight of the at least one discrete solid dosage form; and 0-5 wt % lubricant based on the total weight of the at least one discrete solid dosage form. The composition preferably delivers a therapeutically effective amount of tizanidine to a subject at a target range of about 100 micrograms/day to about 700 micrograms/day.

Base and Salt Forms of Tizanidine

Tizanidine hydrochloride (HCl) is currently on the market in the form of tablets for oral use (Zanaflex®), and is a short-acting drug for the management of spasticity. Because of the short duration of effect, treatment with Zanaflex® is reserved for those daily activities and times when relief of spasticity is most important. A dose of 8 mg of Zanaflex® reduces muscle tone in patients with spasticity. The effect typically peaks at approximately 1 to 2 hours and dissipates between 3 to 6 hours. The dose can be repeated at 6 to 8 hour intervals, as needed, to a maximum of three doses in 24 hours.

Figure 6:
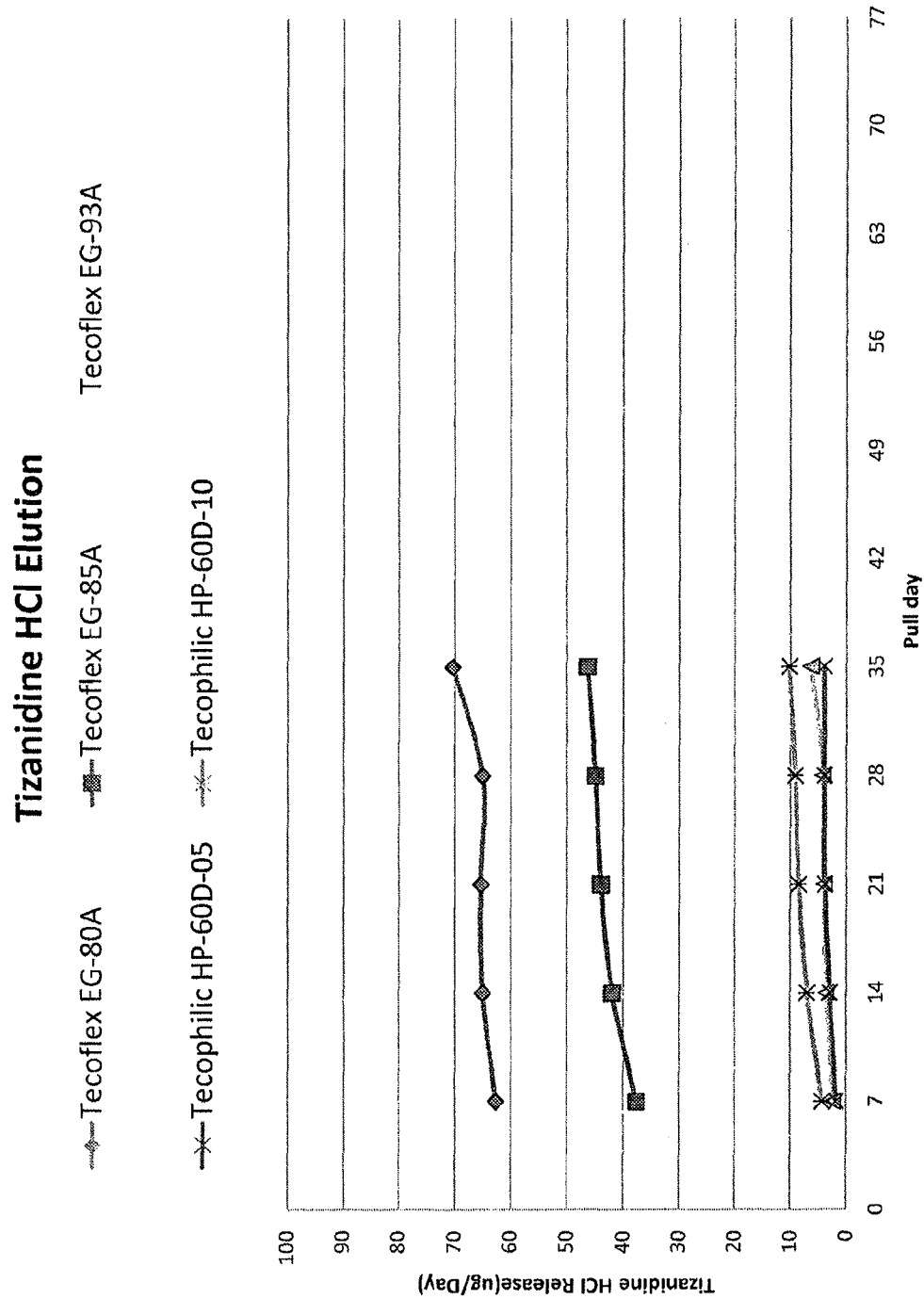
FIG. 6 is a graph showing the in vitro elution rate (µg/day) of tizanidine from implants of the present invention comprising tizanidine HCl as described in Example 3.

During the development of the present invention, it was discovered that when tizanidine HCl was used as the API salt in the implantable drug delivery compositions, the elution rate in vitro was below 100 µg per day for all polyurethanes investigated (see e.g, Example 3 below and FIG. 6). Thus, although tizanidine HCl has been a preferred salt form for oral dosage forms of tizanidine, it did not prove to be a suitable salt form when placed in implantable drug delivery compositions of the present invention. However, the applicant discovered that the drug release from the implants was about 10- to 15-fold higher when tizanidine free base was used the API in the implantable drug delivery compositions, instead of tizanidine HCl, even at lower API loading, e.g., 250 mg tizanidine free base vs. 380 mg tizanidine HCl (see, e.g., FIGS. 6 and 7). The applicant therefore discovered that tizanidine free base possesses unexpectedly advantageous properties, particularly in comparison to tizanidine HCl, as a form of tizanidine that can be used in a new route of administration, namely, in implantable drug delivery compositions that can deliver a therapeutically effective amount of tizanidine.

Reservoir-Based Drug Delivery Composition

The drug delivery composition is a reservoir-based drug delivery composition. As used herein, the "reservoir-based composition" is intended to encompass a composition having a substantially or completely closed, surrounded, or encased hollow space or reservoir, where the hollow space or reservoir is filled, at least partially, with at least one discrete solid dosage form.

In one embodiment of the present invention, a drug delivery composition comprises a drug elution rate-controlling excipient comprising an elastomeric polymer defining a reservoir, and the reservoir contains at least one discrete solid dosage form comprising tizanidine free base. The elastomeric polymer defining the reservoir is formed separate from the at least one discrete solid dosage form (i.e., the elastomeric polymer defining the reservoir and the at least one discrete solid dosage form are not two "layers" that are bonded to each other; rather, the elastomeric polymer defining the reservoir is separately formed and the at least one discrete solid dosage form is placed into contact with the elastomeric polymer when it is loaded into the reservoir).

Figure 3:
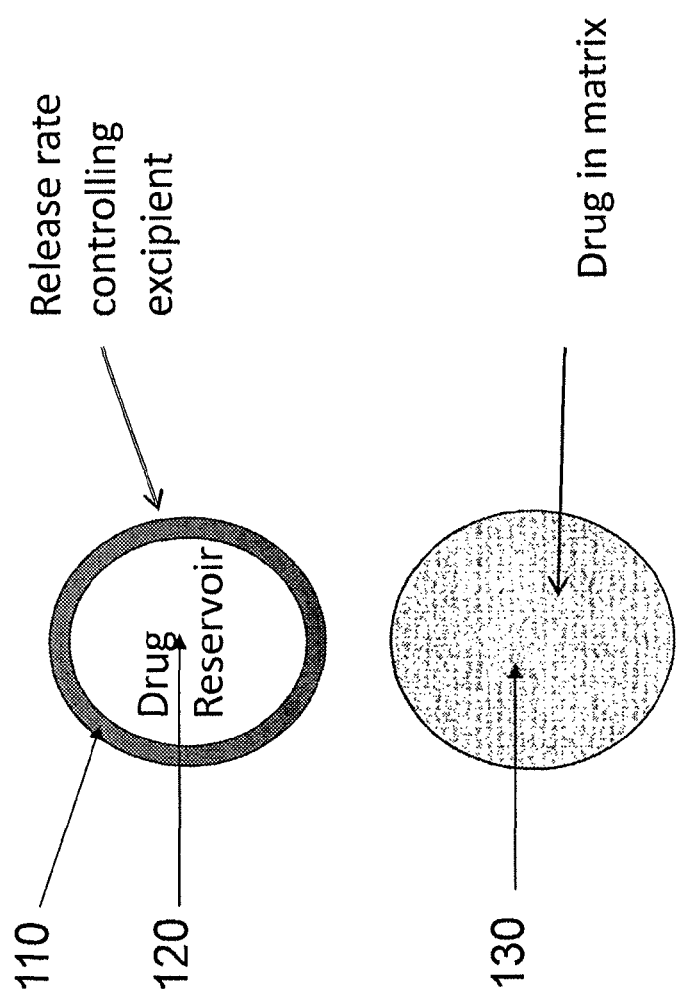
FIG. 3 depicts the difference between a drug reservoir and a matrix-based implant.

A reservoir-based composition, as used herein, is in contradistinction to a matrix-based composition. As depicted in FIG. 3, a drug reservoir includes a reservoir portion 120 and a rate controlling portion (excipient 110) whereas a matrix-based implant only consists of the matrix material 130 with the drug incorporated therein. In other words, in a reservoir system, the drug is contained within or is surrounded by some type of rate-controlling material (e.g., a wall, membrane, or casing). In a matrix system, the drug is combined within some type of matrix, often polymeric, which often erodes or degrades in order to release the active to the subject.

Thus, there are some major distinctions between the two types of systems. The reservoir-based system allows for a much higher drug loading (e.g., on the order of 98% maximum) whereas a matrix-based system contains a much smaller amount (e.g., on the order of 25% maximum). Although a higher drug loading may be beneficial, it can also be dangerous because of the increased risk of drug overdose or dumping into the subject if the surrounding material were to break or rupture. Additionally, the reservoir-based composition of the present invention allows for a pseudo-zero order rate (e.g., zero order rate) of release of the active. A matrix-based system, on the contrary, provides for a first order rate of release. A first order rate may be characterized by a high initial rate of release that decays or diminishes quickly over time.

As used herein, the term "pseudo-zero order" or "pseudo-zero order rate" refers to a zero-order, near-zero order, substantially zero order, or controlled or sustained release of an API. A zero order release profile may be characterized by release of a constant amount of the API per unit time. A pseudo-zero order release profile may be characterized by approximating a zero-order release by release of a relatively constant amount of the API per unit time (e.g., within 40%, 30%, 20%, or 10% of the average value). Under a pseudo-zero order rate, the composition may initially release an amount of the API that produces the desired therapeutic effect, and gradually and continually release other amounts of the API to maintain the level of therapeutic effect over an extended period of time (e.g., at least one month, six months, one year, or more than one year). In order to maintain a near-constant level of API in the body, the API may be released from the composition at a rate that will replace the amount of API being metabolized and/or excreted from the body. It will be appreciated by one of ordinary skill in the art that there may be some initial period of time before steady state is reached (e.g., a ramp up or an initial spike before the target range is reached, as shown, for example, in FIGS. 4, 5 and 7 prior to about day 14), which still complies with the present definition of "pseudo-zero order."

Without wishing to be bound to a particular theory, it is believed that a concentration gradient occurs where the concentration of API within the reservoir is "infinite" (e.g., the reservoir acts an infinite supply, but the concentration is practically limited by the amount of active for the given duration of release) and the concentration outside the drug delivery composition is zero (e.g., the subject acts as an infinite sink where the active is constantly being taken away from the composition by the subject's body, such as circulatory, lymphatic systems, etc.). Additionally, the excipient 110 (e.g., the wall through which the active passes) becomes fully saturated with the active ingredient at steady state. Accordingly, this gradient allows the "infinite" supply of API to be adsorbed into the excipient, dissolve in and diffuse through the polymer wall, and then be desorbed for release into the subject. The selection of the excipient 110 may help to provide the pseudo-zero order release of the drug. Without wishing to be limited or bound by any theory, it is believed that the release of the drug is not dependent on the desorption from the excipient.

Dosage Form(s)

The drug delivery composition comprises at least one dosage form comprising at least one API. In one embodiment of the present invention, the drug delivery composition comprises at least one discrete solid dosage form comprising tizanidine free base surrounded by an excipient comprising at least one polymer.

As used herein, the term "discrete solid dosage form" is intended to encompass any dosage form that is in the form of a solid. The solid dosage form may include any cohesive solid form (e.g., compressed formulations, pellets, tablets, etc.) The solid dosage form may include a solid body or mass comprising the API, which may be prepared in any suitable manner known to one of ordinary skill in the art (e.g., compressed, pelleted, extruded).

The solid dosage forms are "discrete" in that there are one or more dosage forms contained within the reservoir. In other words, the discrete solid dosage form includes one or more solid formulations which are separate and distinct from the polymeric rate-controlling excipient. In an exemplary embodiment, the discrete solid dosage form(s) do not fill the entire reservoir or cavity (e.g., the solid dosage forms are substantially cylindrical and the reservoir is substantially cylindrical). For example, the solid dosage form need not be co-extruded with the surrounding excipient such that the solid dosage form fills the entire cavity.

According to one embodiment of the present invention, the discrete solid dosage forms in the drug delivery composition (i.e., all of the discrete solid dosage forms together) comprise a total of about 100 mg to about 600 mg of the tizanidine free base. For example, the discrete solid dosage form(s) may comprise between about 150 mg to about 400 mg tizanidine free base, or about 200 mg to about 300 mg tizanidine free base.

The discrete solid dosage forms may be of any suitable shape and of any suitable quantity. In one embodiment of the present invention, the discrete solid dosage forms are cylindrical in shape. In another embodiment of the present invention, the discrete solid dosage forms are substantially spherical in shape. The discrete solid dosage form(s) may be "substantially spherical" in that the solid dosage forms are spherical or nearly spherical in that the length of the longest radius is approximately equal to the shortest radius of the dosage form. For example, the shape of the dosage form may not deviate from a perfect sphere by more than about 10%. In another embodiment, the discrete solid dosage forms comprise more than one pellet (e.g., 2-12 pellets). The number of discrete solid dosage forms may be proportional to the elution rate. In other words, a higher number of dosage forms may result in a higher average elution rate than a smaller number of dosage forms. Thus, it may be preferable to include more discrete solid dosage forms to give a higher elution rate (e.g., 7-12 pellets).

The number of discrete solid dosage forms (e.g., pellets) may vary depending on the amount of tizanidine free base included in each solid dosage form. For example, each pellet may comprise between about 20 mg to about 60 mg tizanidine free base, or between about 30 mg to about 55 mg tizanidine free base, or between about 40 mg to about 50 mg tizanidine free base.

The discrete solid dosage form(s) comprise tizanidine free base, and optionally, other active pharmaceutical ingredient(s). Tizanidine, which is an imidazoline central α₂-adrenoceptor agonist, is also known as 5-chloro-N-(4,5-dihydro-1H-imidazol-2-yl)benzo[c][1,2,5]thiadiazol-4-amine and has the following general formula:

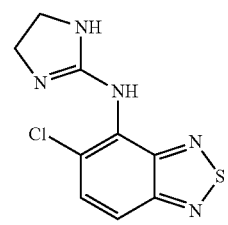

Reference herein to delivery, release, or elution of tizanidine from an implant may include delivery, release, or elution of tizanidine free base and/or active metabolites thereof. The amount of tizanidine free base in compositions of the present invention is not particularly limited, but may be preferably on the order of about 75-97 wt % of the solid dosage form or 85-95 wt % of the solid dosage form (e.g., about 88 wt %). The discrete solid dosage form may optionally include at least one other active pharmaceutical ingredient(s).

The discrete solid dosage form may also comprise a sorption enhancer. As used herein, the term "sorption enhancer" is intended to encompass compounds which improve release of the API from the drug delivery composition. Without wishing to be bound to a particular theory, the sorption enhancers may improve release of the API from the drug delivery composition by drawing water or other fluids into the reservoir from the subject, disintegrating or breaking apart the discrete solid dosage form(s), and/or allowing the API to come into contact or remain in contact the inner walls of the excipient. Such a mechanism may be depicted, for example, in FIG. 1. FIG. 1 represents the rate-controlling excipient 110. The API, located in the reservoir on the left side of the diagram, is sorbed 112 from the reservoir to the excipient. The API then crosses through the excipient 110. The API is then desorbed 114 from the excipient into the subject.

Any suitable sorption enhancer(s) may be selected by one of ordinary skill in the art. Particularly suitable sorption enhancer(s) may include, for example, negatively-charged polymers, such as croscarmellose sodium, sodium carboxymethyl starch, sodium starch glycolate, sodium acrylic acid derivatives (e.g., sodium polyacrylate), cross-linked polyacrylic acid (e.g., CARBOPOL®), chondroitin sulfate, poly-glutamic acid, poly-aspartic acid, sodium carboxymethyl cellulose, neutral polymers, such as polyethylene glycol, polyethylene oxide, polyvinylpyrrolidone, and combinations thereof. In an exemplary embodiment, the sorption enhancer is croscarmellose sodium. The amount of the sorption enhancer may be present on the order of about 1-25 wt % of the solid dosage form, about 2-20 wt % of the solid dosage form, about 2-12 wt % of the solid dosage form, about 5-10 wt % of the solid dosage form (e.g., about 5 wt % or about 10 wt % of the solid dosage form).

The amount of sorption enhancer may be proportional to the elution rate. In other words, a higher weight percent of sorption enhancer in the drug composition may result in a higher average elution rate than a smaller weight percentage. Thus, it may be preferable to include a higher weight percent of sorption enhancer to give a higher elution rate (e.g., 8-25 wt %).

The discrete solid dosage form may also comprise other ingredients as long as they do not adversely impact the elution rate. Other suitable ingredients may include, for example, lubricants, excipients, preservatives, etc. A lubricant may be used in the pelleting or tableting process to form the discrete solid dosage form(s), as would be well known by one of ordinary skill in the art. Suitable lubricants may include, but are not limited to, magnesium stearate, calcium stearate, zinc stearate, stearic acid, polyethylene glycol, and the like. The amount of any additional ingredients is not particularly limited, but is preferably on the order of less than about 5 wt % of the solid dosage form, and most preferably less than about 3 wt % of the solid dosage form, particularly preferably about 2% or less of the solid dosage form.

In one embodiment of the present invention, the at least one discrete solid dosage form comprises, consists essentially of, or consists of: about 75-97 wt % tizanidine free base based on the total weight of the at least one discrete solid dosage form; about 1-25 wt % of at least one sorption enhancer based on the total weight of the at least one discrete solid dosage form; and about 0-5 wt % lubricant based on the total weight of the at least one discrete solid dosage form. For example, the at least one discrete solid dosage form comprises, consists essentially of, or consists of: about 85-95 wt % (e.g., 88 wt %) tizanidine free base based on the total weight of the at least one discrete solid dosage form; about 5-20 wt % (e.g., 10 wt %) of croscarmellose sodium based on the total weight of the at least one discrete solid dosage form; and about 0-5 wt % (e.g., 2 wt %) stearic acid based on the total weight of the at least one discrete solid dosage form. Preferably, each component of the drug delivery composition is provided in an amount effective for the treatment of one or more symptoms of spasticity.

Excipient

The discrete solid dosage form(s) is/are surrounded by an excipient. In other words, the discrete solid dosage form(s) is/are substantially or completely surrounded, encased, or enclosed by the excipient. In the present invention, there are no holes or pores in the excipient to allow egress of the API or ingress of bodily fluids, unlike an osmotic system, which requires a hole to allow release of the API. Moreover, there is no (or negligible) build up of pressure within a drug delivery composition in accordance with the present invention, unlike an osmotic system, which requires pressure to force the API out of the device.

In one embodiment of the present invention, the excipient is substantially or completely non-porous. "Substantially nonporous" may refer to a material which has a porosity or void percentage less than about 10%, about 5%, or about 1%, for example. In particular, the excipient is substantially nonporous in that there are no physical pores or macropores, which would allow for egress of the API from the drug delivery composition. In another embodiment, the excipient is practically insoluble in water. Solubility is the concentration of a solute when the solvent has dissolved all the solute that it can at a given temperature (e.g., the concentration of solute in a saturated solution at equilibrium). As used herein, the term "practically insoluble in water" is consistent with the definition in The United States Pharmacopeia—National Formulary (USP-NF) definition, which provides for more than 10,000 parts solvent to one part solute (e.g., one gram of the excipient in greater than 10,000 mL of water).

Without wishing to be bound to a particular theory, it is believed that a concentration gradient across the excipient (e.g., wall, membrane, layer) allows for continuous release of the API. As depicted in FIG. 1, sorption 112 of the API occurs from the reservoir onto the rate-controlling excipient 110. The API then dissolves into and fully saturates the excipient 110, diffuses through it, and the API is then desorbed 114 from the excipient into the subject. Accordingly, this gradient allows the "infinite" supply of API to be adsorbed onto the excipient, diffuse through it and desorbed into the subject, which, based on the excipient selected, may help to provide the pseudo-zero order release of the drug. Thus, the excipient may also be called a drug elution rate-controlling or rate-controlling excipient herein. The "rate-controlling excipient" is intended to encompass materials which control the elution rate of the API. In other words, a polymeric excipient, that when encasing the drug delivery composition, provides a different rate of release, namely, a controlled rate of release (e.g., pseudo-zero order) as compared to the release of an API from an identical composition without a rate-controlling excipient.

Figure 2:
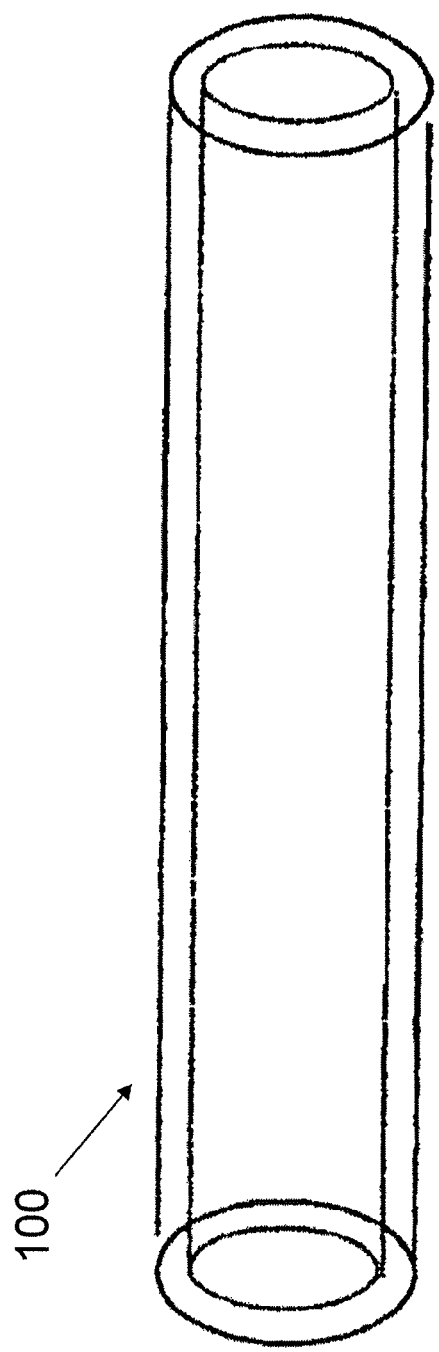
FIG. 2 depicts the cylindrical shape of a reservoir-based drug delivery composition according to one embodiment of the present invention.

The excipient defines the shape of the reservoir. The reservoir may be of any suitable size and shape. In an exemplary embodiment, the excipient is substantially cylindrically shaped. As used herein, the terms "cylindrical" or "cylindrically shaped" may be used interchangeably to mean at least substantially having the shape of a cylinder. As used herein, the term "cylinder" includes and refers to, but is not limited to: circular cylinders, having a circular cross-section; elliptical cylinders, having an elliptical cross-section; generalized cylinders, having any shape in cross-section; oblique cylinders, in which the end surfaces are not parallel to one another and/or are not normal to the axis of the cylinder; and conical and frusto-conical analogs thereof. In accordance with one aspect of the invention, a hollow tube may include a substantially consistent cross-sectional area and two substantially equally-sized circular ends. The cylindrical shape defines the shape of the excipient defining the reservoir (e.g., the outer portion of the drug delivery composition). An embodiment of the cylindrically shaped excipient is depicted, for example, in FIG. 2. Preferably, the dimensions of the cylindrical hollow tube should be as precise as possible (e.g., a consistent shape and dimension along the length of the tube, in particular, a consistent circular cross-section). The reservoir may be of any suitable size depending on the active and location of delivery. For example, the composition may range in size from about 2 mm to about 5 mm in diameter (e.g., about 2.7 mm or about 4 mm in diameter) and about 6 mm to about 70 mm in length, for example about 20 mm to about 50 mm in length, in one embodiment about 45 mm in length.

The excipient comprises at least one polymer. Any suitable polymer may be selected by one of ordinary skill in the art, as long as the polymer allows for delivery of a therapeutically effective amount of the API to the subject, for example, at a pseudo-zero order rate, for the intended period of time that the implant resides in a patient. In one embodiment, the polymer comprises a thermoplastic elastomer. As used herein, "thermoplastic," "thermoplastic elastomers (TPE)" or "thermoplastic rubbers" may be used to denote a class of copolymers or a physical mix of polymers (e.g., a plastic and a rubber), which consist of materials with both thermoplastic and elastomeric properties. The crosslinking in thermoplastic elastomeric polymers may include a weaker dipole or hydrogen bond or the crosslinking occurs in one of the phases of the material. The class of copolymer may include, for example, styrenic block copolymers, polyolefin blends, elastomeric alloys, thermoplastic polyurethanes, thermoplastic copolyester, and thermoplastic polyamides.

As used herein, "elastomer" or "elastomeric polymer" is intended to encompass polymers (homopolymers, copolymers, terpolymers, oligomers, and mixtures thereof) having elastomeric properties (e.g., the tendency to revert to its original shape after extension). In other words, the polymeric backbone may contain one or more elastomeric subunits (e.g., an elastomeric soft segment or block). In one embodiment, the elastomeric polymer comprises polyurethane, polyether, polyamide, polycarbonate, polysilicone, or copolymers thereof. Thus, the elastomeric polymer may include polyurethane-based polymers, polyether-based polymers, polysilicone-based polymers, polycarbonate-based polymers, or combinations thereof.

The polymer may be formed by any suitable means or techniques known to one of ordinary skill in the art. For example, the polymer may be formed from monomers, polymer precursors, pre-polymers, polymers, etc. Polymer precursors may include monomeric as well as oligomeric substances capable of being reacted or cured to form polymers. The polymers may be synthesized using any suitable constituents.

In one embodiment of the present invention, the polymer comprises polyurethanes (e.g., comprising a urethane linkage, —RNHCOOR'—). Polyurethanes may include polyether-based polyurethanes, polycarbonate-based polyurethanes, polyamide-based polyurethanes, polysilicone-based polyurethanes, or the like. Polyurethanes may be formed, for example, from polyols (e.g., comprising two or more hydroxyl or alcohol functional groups, —OH), isocyanates (e.g., comprising an isocyanate group, —N=C=O), and, optional chain extenders, catalysts, and other additives.

Suitable polyols may include, for example, polyether polyols, polycarbonate-based polyols, and the like, which may include diols, triols, etc. Polyether polyols may include, for example, polyalkylene glycols (e.g., polyethylene glycols, polypropylene glycols, polybutylene glycols), poly(ethylene oxide) polyols (e.g., polyoxyethylene diols and triols), polyoxypropylene diols and triols, and the like. Alternative polyols may include, for example, 1,4-butanediol, 1,6-hexanediol, 1,12-dodecanediol, and the like.

For example, the polyol segment or segments may be represented by one or more of the following formulas:

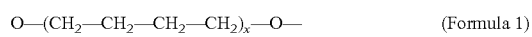

O—(CH$_2$—CH$_2$—CH$_2$—CH$_2$)$_x$—O— (Formula 1)

—[O—(CH$_2$)$_n$]$_x$—O— (Formula 2)

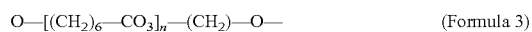

O—[(CH$_2$)$_6$—CO$_3$]$_n$—(CH$_2$)—O— (Formula 3)

Formula (1) may depict a suitable polyether-based polyol, which may be representative of a polyol to produce TECOFLEX® polyurethanes. Formula (2) may depict a suitable polyether-based polyol, which may representative of a polyol to produce TECOPHILIC® polyurethanes. Formula (3) may depict a suitable polycarbonate-based polyol, which may be representative of a polyol to produce CARBOTHANE® polyurethanes (all of which are obtainable from the Lubrizol Corporation with offices in Wickliffe, Ohio). The polyols may also include mixtures of one or more types of polyol segments.

Suitable isocyanates may include, for example, aliphatic and cycloaliphatic isocyanates, as well as aromatic isocyanates, such as 1,6-hexamethylene diisocyanate (HDI), 1-isocyanato-3-isocyanatomethyl-3,5,5-trimethyl-cyclohexane (isophorone diisocyanate, IPDI), and 4,4'-diisocyanato dicyclohexylmethane (H12MDI), as well as methylene diphenyl diisocyanate (MDI) and toluene diisocyanate (TDI).

Suitable chain extenders may include, for example, ethylene glycol, 1,4-butanediol (1,4-BDO or BDO), 1,6-hexanediol, cyclohexane dimethanol, and hydroquinone bis(2-hydroxyethyl)ether (HQEE).

In one embodiment of the present invention, the polymer comprises a polyether-based polyurethane. For example, the polymer may be an aliphatic polyether-based polyurethane comprising poly(tetramethylene oxide) and polymerized 4,4'-diisocyanato dicyclohexylmethane (H12MDI) and 1,4-butanediol. An exemplary type of suitable polyether-based polyurethanes includes TECOFLEX® polymers available from the Lubrizol Corporation. For example, TECOFLEX® polymers include aliphatic block copolymer with a hard segment consisting of polymerized 4,4'-diisocyanato dicyclohexylmethane (H12MDI) and 1,4-butanediol, and a soft segment consisting of the macrodiol poly(tetramethylene oxide). In one embodiment, the TECOFLEX® polymer comprises TECOFLEX® EG-93A polyurethane. In another embodiment, the TECOFLEX® polymer comprises TECOFLEX® EG-80A polyurethane.

In another embodiment of the present invention, the polymer comprises polyether-amides (e.g., thermoplastic poly(ether-block-amide)s, e.g., PEBA, PEB, TPE-A, and commercially known as PEBAX® polyether-amides obtainable from Arkema Chemicals Inc., headquartered in King of Prussia, Pa.). Synthesis may be carried out, for example, in the molten state by polycondensation between polyether blocks (e.g., a diol, such as polyoxyalkylene glycols) and polyamide blocks (e.g., carboxylic acid terminated amide blocks, such as dicarboxylic blocks), which results in a thermoplastic copolymer. The long chain molecules may consist of numerous blocks where the polyamide provides rigidity and the polyether provides flexibility to the polymer. Thus, the polyether-amides may consist of linear chains of hard polyamide (PA) blocks covalently linked to soft polyether (PE) blocks via ester groups. The polyether-amides may also be synthesized via a catalyst (e.g., metallic $Ti(OR)_4$), which facilitates the melt polycondensation of the polyether and polyamide blocks. The general structural formula of these block copolymers may be depicted as follows:

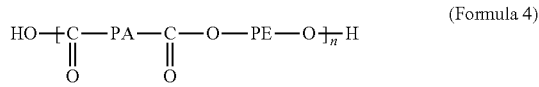

(Formula 4)

The polyamide block may include various amides including nylons (such as nylon 6, nylon 11, nylon 12, etc.). The polyether block may also include various polyethers, such as polytetramethylene oxide (PTMO), polypropylene oxide (PPO), polyethylene glycol (PEG), poly(hexamethylene oxide), polyethylene oxide (PEO), and the like. The ratio of polyether to polyamide blocks may vary from 80:20 to 20:80 (PE:PA). As the amount of polyether increases, a more flexible, softer material may result.

For example, the thermoplastic elastomer may be selected from the group consisting of TECOFLEX® polyurethanes, CARBOTHANE® polyurethanes, PEBAX® polyether-amides, and combinations thereof. For example, the elastomer may include TECOFLEX® EG-93A polyurethane, TECOFLEX® EG-80A polyurethane, TECOFLEX® EG-85A polyurethane, PEBAX® 2533 polyether-amide, PEBAX® 3533 polyether-amide, CARBOTHANE® PC-3585A polyurethane, and combinations thereof.

TECOFLEX® polyurethanes and CARBOTHANE® polyurethanes are described, for example, in Lubrizol's brochure for Engineered Polymers for Medical & Healthcare dated 2011, the disclosure of which is hereby incorporated by reference in its entirety, for all purposes. For example, TECOFLEX® aliphatic polyether polyurethanes may have the following characteristics:

TABLE 1

| Product | Hardness | Flex Modulus | Feature |
|---|---|---|---|
| EG80A | 72A | 1,000 | Clear |
| EG85A | 77A | 2,300 | Clear |
| EG93A | 87A | 3,200 | Clear |
| EG100A | 94A | 10,000 | Clear |
| EG60D | 51D | 13,000 | Clear |
| EG65D | 60D | 37,000 | Clear |
| EG68D | 63D | 46,000 | Clear |
| EG72D | 67D | 92,000 | Clear |
| EG80A B20/B40 | 73A/78A | 1,200/1,500 | Radiopaque |
| EG85A B20/B40 | 83A/86A | 2,700/3,700 | Radiopaque |
| EG93A B20/B40 | 90A/95A | 5,000/4,700 | Radiopaque |
| EG100A B20/B40 | 93A/98A | 17,000/14,000 | Radiopaque |
| EG60D B20/B40 | 55D/65D | 27,000/27,000 | Radiopaque |
| EG65D B20/B40 | 63D/78D | 82,000/97,000 | Radiopaque |
| EG68D B20 | 73D | 76,600 | Radiopaque |
| EG72D B20/B40 | 75D/82D | 125,000/179,000 | Radiopaque |

CARBOTHANE® aliphatic polycarbonate polyurethanes may have the following characteristics, for example:

TABLE 2

| Product | Hardness | Flex Modulus | Feature |
|---|---|---|---|
| PC-3575A | 71A | 620 | Clear |
| PC-3585A | 78A | 1,500 | Clear |
| PC-3595A | 91A | 4,500 | Clear |
| PC-3555D | 52D | 24,000 | Clear |
| PC-3572D | 71D | 92,000 | Clear |
| PC-3575A-B20 | 79A | 860 | Radiopaque |
| PC-3585A-B20 | 81A | 1,700 | Radiopaque |
| PC-3595A-B20 | 90A | 8,600 | Radiopaque |
| PC-3555D-B20 | 54D | 25,000 | Radiopaque |
| PC-3572D-B20 | TBD | 141,000 | Radiopaque |

The polymers may be processed using any suitable techniques, such as extrusion, injection molding, compression molding, spin-casting. For example, the polymer may be extruded or injection molded to produce hollow tubes having two open ends (see e.g., FIG. 2). The hollow tube can be loaded with the discrete solid dosage form(s). The open ends are sealed to form the reservoir-based drug delivery composition. A first open end may be sealed before filling the tube with the discrete solid dosage form(s), and the second open end may be sealed after the tube is filled with all of the discrete solid dosage form(s). The tube may be sealed using any suitable means or techniques known in the art. For example, the ends may be plugged, filled with additional polymers, heat sealed, or the like. The tubes should be permanently sealed such that the discrete solid dosage form(s) may not be removed. Also, the ends should be suitably sealed such that there are no holes or openings that would allow egress of the active once implanted.

The wall thickness of the excipient may be selected to provide for the desired elution rate. The wall thickness may be inversely proportional to elution rate. Thus, a larger wall thickness may result in a lower elution rate. The excipient may form a wall having an average thickness of about 0.05 to about 0.5 mm, or about 0.1 mm to about 0.3 mm (e.g., about 0.1 mm, about 0.2 mm, or about 0.3 mm).

In one embodiment of the present invention, the drug delivery composition does not require erosion or degradation of the excipient in vivo in order to release the API in a therapeutically effective amount. Alternatively, the excipient is not substantially erodible and/or not substantially degradable in vivo for the intended life of the implantable composition. As used herein, "erosion" or "erodible" are used interchangeably to mean capable of being degraded, disassembled, and/or digested, e.g., by action of a biological environment. A compound that is "not substantially erodible" is not substantially degraded, disassembled, and/or digested over time (e.g., for the life of the implant). Alternatively, the material may be "not substantially erodible" or "does not require erosion" in vivo in order to provide for release of the API. In other words, the compound may erode over time, but the API is not substantially released due to erosion of the material. With respect to "degradation" or "degradable," these are intended to mean capable of partially or completely dissolving or decomposing, e.g., in living tissue, such as human tissue. Degradable compounds can be degraded by any mechanism, such as hydrolysis, catalysis, and enzymatic action. Accordingly, a compound that is "not substantially degradable" does not substantially dissolve or decompose over time (e.g., for the life of the implant) in vivo. Alternatively, the material may be "not substantially degradable" or "not requiring degradation" in order to provide for release of the API. In other words, the compound may degrade over time, but the API is not substantially released due to degradation of the material.

Implantation

The method of treating one or more symptoms of spasticity includes implanting a reservoir-based drug delivery composition into a subject. The term "subject" or "patient", used herein, refers to a mammalian subject, such as a human being. The subject is preferably a human that has been diagnosed with spasticity and/or exhibits one or more symptoms of spasticity.

The drug delivery composition may be implanted into the subject in any suitable area of the subject using any suitable means and techniques known to one of ordinary skill in the art. For example, the composition may be implanted subcutaneously, e.g., at the back of the upper arm or the upper back (e.g. in the scapular region). As used herein, the terms "subcutaneous" or "subcutaneously" or "subcutaneous delivery" means directly depositing in or underneath the skin, a subcutaneous fat layer, or intramuscularly. The drug delivery composition may be delivered subcutaneously using any suitable equipment or techniques. In one embodiment, the drug delivery composition is placed subcutaneously in the subject's arm. Alternative sites of subcutaneous administration may also be used as long as a pharmaceutically acceptable amount of the API would be released into the subject in accordance with the present invention. Preferably, the drug delivery composition should not migrate significantly from the site of implantation. Methods for implanting or otherwise positioning the compositions into the body are well known in the art. Removal and/or replacement may also be accomplished using suitable tools and methods known in the art.

Once implanted, the reservoir-based drug delivery composition may systemically deliver a therapeutically effective amount of the tizanidine to the subject at a pseudo-zero order rate (e.g., zero order rate) for a long duration (e.g., a period of time of at least one month). As used herein, the term "systemic" or "systemically" refers to the introduction of the API into the circulatory, vascular and/or lymphatic system (e.g., the entire body). This is in contrast to a localized treatment where the treatment would only be provided to a specific, limited, localized area within the body. Thus, the API is systemically delivered to the subject by implanting the drug delivery composition subcutaneously into the subject.

A therapeutically effective amount of the tizanidine is preferably delivered to the subject at a pseudo-zero order rate. Pseudo-zero order refers to a zero-order, near-zero order, substantially zero order, or controlled or sustained release of the tizanidine. A pseudo-zero order release profile may be characterized by approximating a zero-order release by release of a relatively constant amount of the tizanidine per unit time (e.g., within about 30% of the average value). Thus, the composition may initially release an amount of the tizanidine that produces the desired therapeutic effect, and gradually and continually release other amounts of the tizanidine to maintain the level of therapeutic effect over the intended duration (e.g., about one year). In order to maintain a near-constant level of tizanidine in the body, the tizanidine may be released from the composition at a rate that will replace the amount of tizanidine being metabolized and/or excreted from the body.

Without wishing to be bound to a particular theory, it is believed that the reservoir-based drug composition works by releasing the active (e.g., tizanidine) through the excipient membrane or wall. In other words, the tizanidine diffuses across the excipient, e.g., as depicted in FIG. 1. Thus, sorption 112 of the tizanidine occurs from the reservoir onto the rate-controlling excipient 110. The tizanidine fully saturates the excipient 110 at steady state, and the tizanidine diffuses through the excipient and is then desorbed 114 from the excipient into the subject at a pseudo-zero order rate.

The therapeutically effective amount of the tizanidine may be delivered to the subject at a target range between a maximum value and a minimum value of average daily elution rate for the API. As used herein, the term "elution rate" refers to a rate of API delivery, which is based on the oral dose rate multiplied by the fractional oral bioavailability, which may be depicted as follows:

Oral Dose×Fractional Oral Bioavailability %=Target Elution Rate(mg/day)

The elution rate may be an average rate, e.g., based on the mean average for a given period of time, such as a day (i.e., average daily elution rate). Thus, a daily elution rate or average daily elution rate may be expressed as target daily oral dosage multiplied by oral bioavailability. For example, in the case of the oral dosage form of tizanidine HCl, which has an approximate oral bioavailability of 20-40% and a target oral daily dose of 2 mg/day going to 12 mg/day, a target daily elution rate for tizanidine is about 400 micrograms per day to about 4,800 micrograms per day.

The maximum and minimum values refer to a maximum average daily elution rate and a minimum average daily elution rate, respectively. The minimum value required for a pharmaceutically effective dose may be correlated to or determined from a trough value for an oral dosage version of the API (e.g., based on the blood/plasma concentrations for oral formulations). Similarly, maximum value may be correlated to or determined from the peak value for an oral dosage version of the API (e.g., the maximum blood/plasma concentration when an oral dosage is first administered or a pharmaceutically toxic amount). In other words, the target range is a range between maximum and minimum average daily elution rates, respectively, which may be determined based on blood/plasma concentrations for equivalent oral dosage forms containing the same active. For example, the oral dosage form of tizanidine HCl has an approximate minimum elution rate of 100 micrograms per day, and an approximate maximum elution rate of 10,000 micrograms per day.

In one embodiment of the present invention, tizanidine is delivered to the subject at a target range of about 100 micrograms/day to about 10,000 micrograms/day. For example, tizanidine is delivered to the subject at a target range of about 100 to about 5,000 micrograms/day, or about 200 to about 4,000 micrograms per day, or about 300 to about 3,000 micrograms per day or about 400 to about 2,000 micrograms per day. The testing method set forth in the examples to determine the elution rates for compositions comprising tizanidine includes placing the implants in an elution bath consisting of PBS or 0.9% saline at 37° C. Weekly exchanges of the elution media are then analyzed by HPLC for the durations given.

Figure 4:
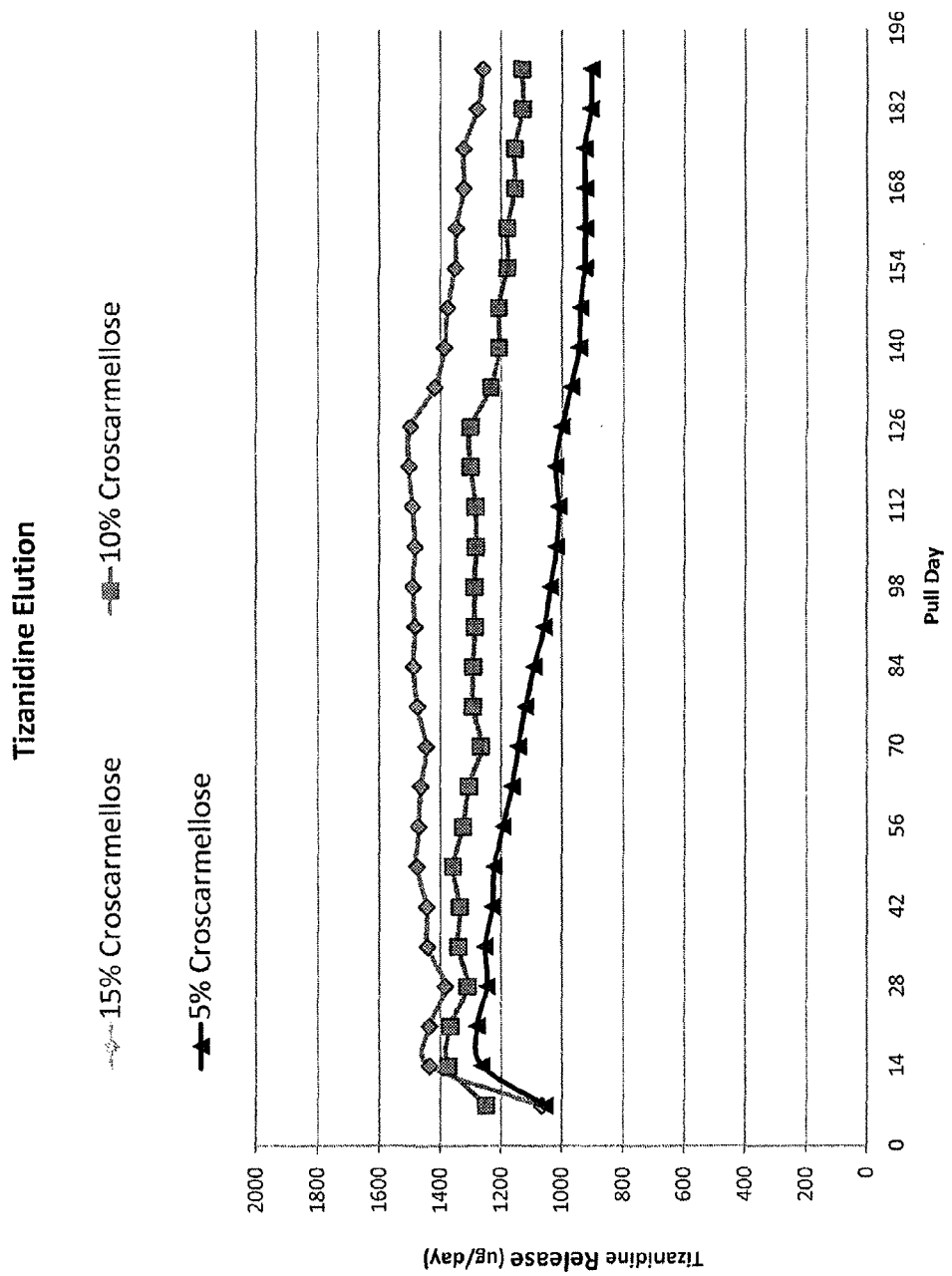
FIG. 4 is a graph showing the in vitro elution rate (µg/day) of tizanidine from implants of the present invention comprising tizanidine free base and varying amounts of a sorption enhancer according to embodiments of the present invention described in Example 1.
Figure 5:
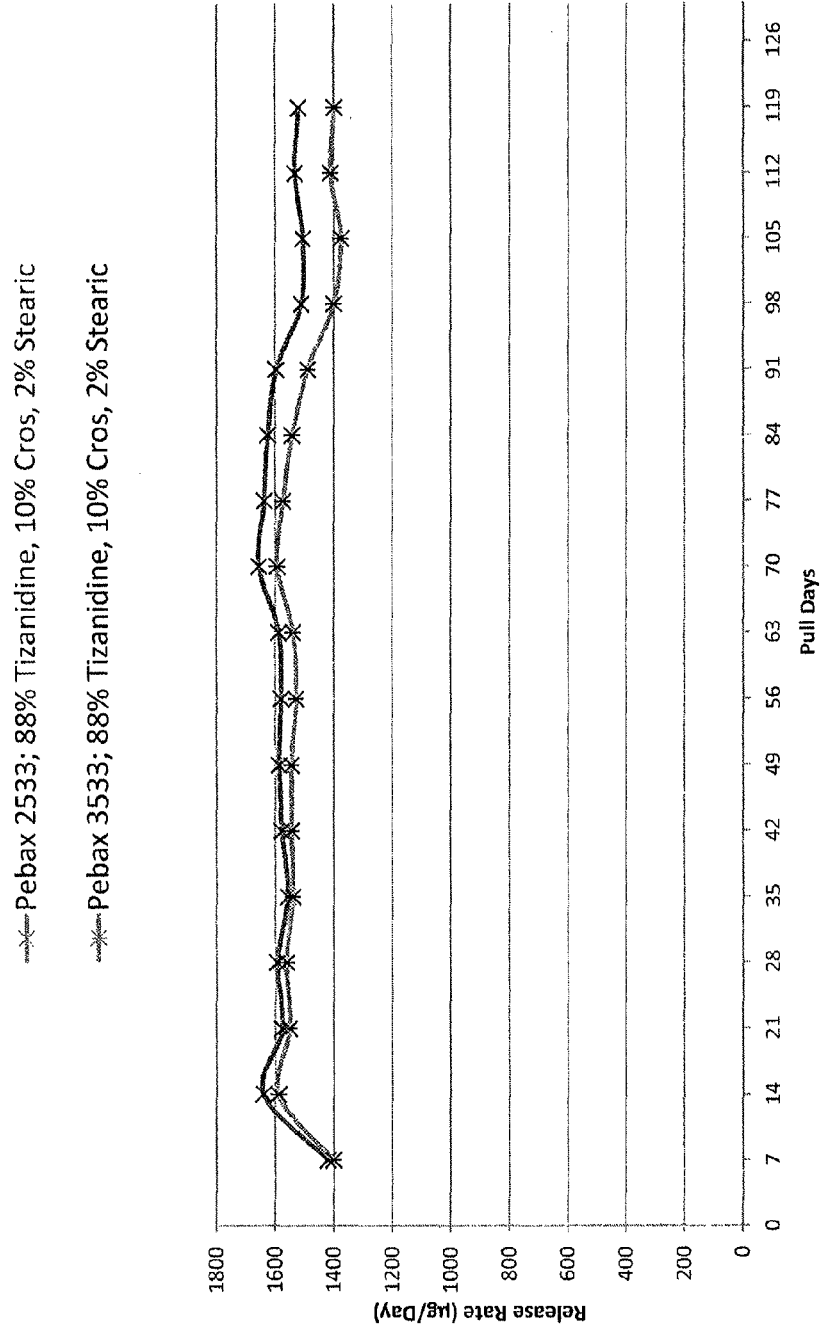
FIG. 5 is a graph showing the in vitro elution rate (µg/day) of tizanidine from PEBAX® implants of the present invention comprising tizanidine free base, according to embodiments of the present invention described in Example 2.
Figure 7:
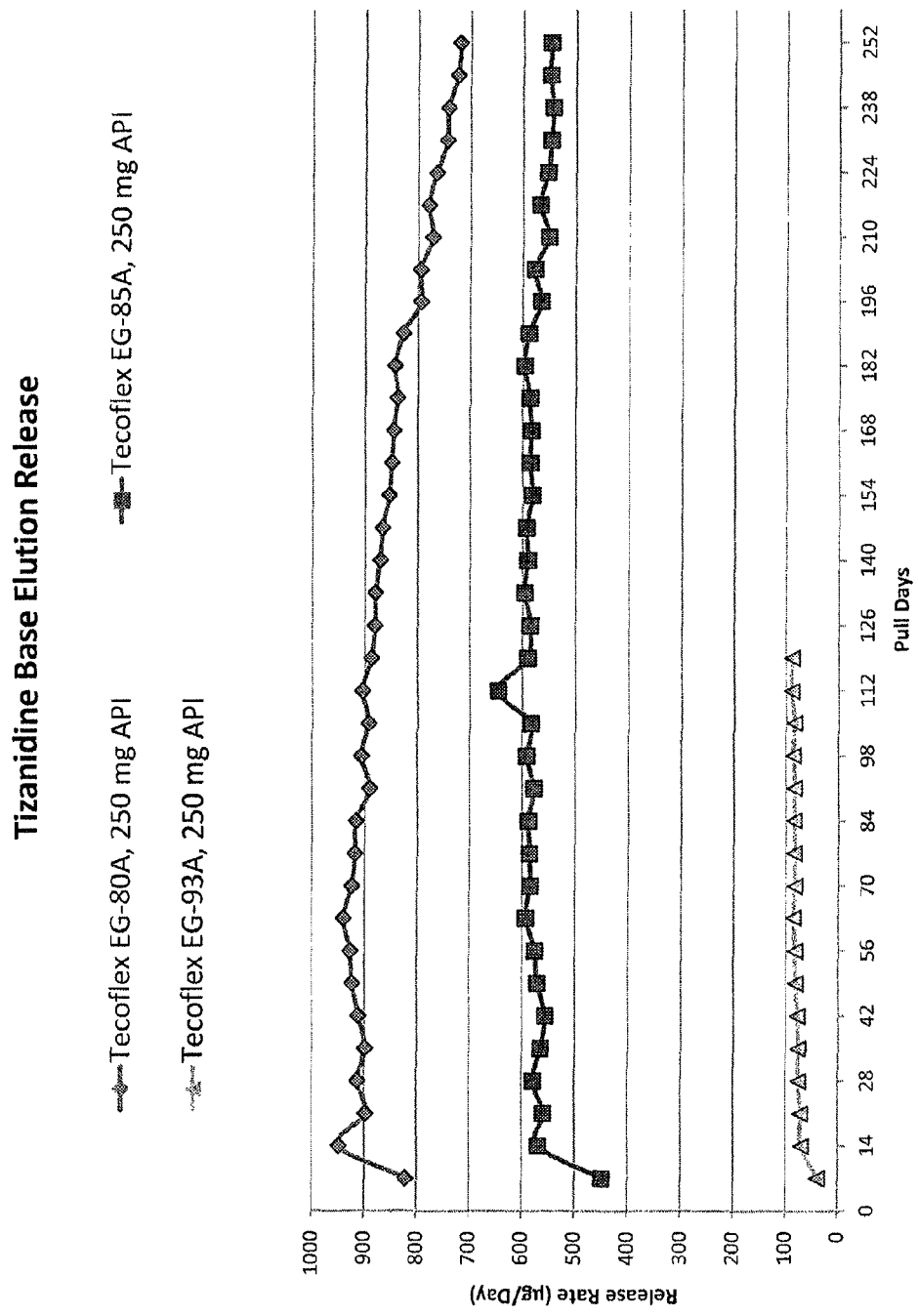
FIG. 7 is a graph showing the in vitro elution rate (µg/day) of tizanidine from implants of the present invention comprising tizanidine free base as described in Example 4.

The drug delivery compositions of the present invention are long-lasting. In other words, the tizanidine is delivered to the subject (e.g., at a pseudo-zero order rate) for an extended period of time. For example, the tizanidine is delivered to the subject for at least about one month (about one month or greater), at least about three months (about three months or greater), at least about six months (about six months or greater), at least about one year (about one year or greater), at least about 18 months (about 18 months or greater), at least about two years (about two years or greater), at least about 30 months (about 30 months or greater), or any period of time within those ranges. FIGS. 4, 5, and 7, for example, show in vitro elution rates of tizanidine at a pseudo-zero order rate over several weeks.

According to one embodiment, a method of treating one or more symptoms of spasticity comprises implanting a reservoir-based drug delivery composition into a subject to systemically deliver a therapeutically effective amount of tizanidine to the subject for a period of time of from about one month to about two years, wherein the drug delivery composition comprises at least one discrete solid dosage form comprising tizanidine free base surrounded by an excipient comprising at least one polymer, at an average daily elution rate of about 100 micrograms/day to about 10,000 micrograms/day, wherein the at least one discrete solid dosage form comprises, consists essentially of, or consists of 75-97 wt % tizanidine free base (e.g., about 88% tizanidine free base), 1-25 wt % of at least one sorption enhancer (e.g., about 10% croscarmellose sodium), and 0-5 wt % lubricant (e.g., about 2% stearic acid), all based on the total weight of the at least one discrete solid dosage form.

Prior to implantation, the drug delivery composition may undergo any suitable processing, such as sterilization (such as by gamma radiation), heat treatment, molding, and the like. Additionally, the drug delivery composition may be conditioned or primed by techniques known in the art. For example, the drug delivery composition may be place in a medium (e.g., an aqueous medium, such as saline). The medium, priming temperature, and time period of priming can be controlled to optimize release of the active upon implantation.

Efficacy of Treatment for Spasticity

The methods of treatment described herein may treat, delay onset, suppress, or inhibit one or more symptoms of spasticity. A pharmaceutically effective or therapeutic amount of tizanidine should be administered sufficient to effect or produce the desired therapy. For example, releasing an amount of tizanidine effective to inhibit or suppress one or more symptoms of spasticity (e.g., involuntary tension, stiffening or contraction of muscles) is desired. A doctor would be able to determine the efficacy of the treatment (i.e., know the tizanidine was working to treat symptoms of spasticity) using techniques known to one of ordinary skill in the art.

For example, after a subject has begun a regimen of tizanidine, a clinician may conduct a clinical examination to assess strength and reflexes, using rating scales such as the Ashworth Scale or Modified Ashworth Scale (which provide an objective score of muscle tone based on range of motion). Alternatively, the clinician may make functional measurements using assessments such as the Fugl-Meyer Assessment, which provides an objective score based on motor functioning, balance, sensation and joint functioning. Improvement in a subject's symptoms, as measured by a clinician according to the aforementioned assessments, or other assessments used in the art to evaluate the symptoms of spasticity, can be used to indicate whether the amount of tizanidine being used is effective.

It would also be appreciated by one of ordinary skill in the art that the treatment regime for treating one or symptoms of spasticity with tizanidine may depend on a variety of factors, including the type, age, weight, sex, diet and medical condition of the subject. Thus, the treatment regime actually employed may vary widely from subject to subject.

Subcutaneous Delivery Systems and Kits

In one aspect of the present invention, a subcutaneous delivery system comprises an elastomeric reservoir implant comprising at least one discrete solid dosage form surrounded by a polymeric rate-controlling excipient. The at least one discrete solid dosage form comprises tizanidine free base. The subcutaneous delivery system provides for release of the tizanidine at an elution rate suitable to provide a therapeutically effective amount of the tizanidine to a subject at a pseudo-zero order rate for a period of time of at least one month. In another aspect of the present invention, a kit for subcutaneously placing a drug delivery composition comprises a reservoir-based drug delivery composition comprising a polymeric rate-controlling excipient defining a reservoir containing at least one discrete solid dosage form comprising tizanidine free base; and an implanter for inserting the reservoir-based drug delivery composition beneath the skin.

The drug delivery composition may be implanted into the subject in any suitable area of the subject using any suitable means and techniques known to one of ordinary skill in the art. For example, the composition may be implanted subcutaneously, e.g., at the back of the upper arm, by directly depositing in or underneath the skin, a subcutaneous fat layer, or intramuscularly.

The drug delivery composition may be delivered subcutaneously using any suitable equipment or techniques, e.g., an implanter known to one ordinary skill in the art. The kits may comprise the drug delivery composition pre-loaded into the implanter or the drug delivery composition may be loaded by the doctor or other user. The implanter may be an implantation device, such as a syringe, cannula, trocar or catheter, that may be inserted into an incision made at the delivery site of the subject. Suitable implantation devices and implantation methods include the trocar and methods disclosed in U.S. Pat. No. 7,214,206 and U.S. Pat. No. 7,510,549, the disclosures of which are herein incorporated by reference in their entirety, for all purposes. Other suitable methods for implanting or otherwise positioning the compositions into the body, e.g., by a doctor, are well known in the art. Removal and/or replacement may also be accomplished using suitable tools and methods known in the art. Kits may also comprise other equipment well known in the art, such as scalpels, clamps, suturing tools, hydration fluid, and the like.

Implantable Drug Delivery Compositions with Polymer Excipient(s)

Without wishing to be bound to a particular theory, it is believed that by selecting specific polymers with certain contents or ratios of hard to soft segments, certain desired elution rates may be achieved. Moreover, by adding certain sorption enhancers in certain amounts with the tizanidine to the discrete solid dosage formulations within the reservoir, the elution rates may be further changed or modulated (e.g., "tuned" or "dialed in") from the drug delivery composition to desired, pharmaceutically efficacious values.

According to one aspect of the present invention, a method of delivering a therapeutically effective amount of tizanidine from an implantable drug delivery composition comprises implanting a reservoir-based drug delivery composition into a subject to systemically deliver a therapeutically effective amount of tizanidine to the subject at a pseudo-zero order rate (e.g., zero order rate) for a period of time of at least one month. The drug delivery composition comprises at least one discrete solid dosage form surrounded by an excipient comprising at least one polymer, and the at least one discrete solid dosage form comprises tizanidine free base. The polymer comprises a substantially non-porous, elastomeric polymer comprising soft and hard segments, and the relative content of the soft and hard segments provide an elution rate within a target range between a maximum and minimum value of a desired average daily elution rate for the tizanidine.

According to one embodiment of the present invention, a drug delivery composition includes a rate-controlling excipient defining a reservoir which contains at least one discrete solid dosage form comprising tizanidine free base. The rate-controlling excipient comprises a substantially non-porous, elastomeric polymer comprising soft and hard segments selected based on the relative content of soft and hard segments of the polymer to obtain an elution rate within a target range of average daily elution rate for the tizanidine. The at least one discrete solid dosage form comprises at least one sorption enhancer in an amount effective to modulate the average daily elution rate of the tizanidine to provide for release of the tizanidine at pseudo-zero order within the target range at the therapeutically effective amount for a period of time of at least one month. The amount of sorption enhancer may be directly proportional to the average daily elution rate.

According to another embodiment of the present invention, a method of choosing an implantable drug delivery composition comprises selecting a rate-controlling excipient comprising a substantially non-porous, elastomeric polymer comprising soft and hard segments for defining a reservoir based on the relative content of soft and hard segments of the polymer to adjust the elution rate within a target range of average daily elution rate for tizanidine; and selecting and formulating the tizanidine free base and at least one sorption enhancer in order to modulate the elution rate to achieve a therapeutically effective amount of the tizanidine at pseudo-zero order for a period of time of at least one month, wherein the amount of sorption enhancer may be directly proportional to the average daily elution rate.

Polymer Selection

The excipient comprises at least one polymer having soft and hard segments. As used herein, the term "segment" may refer to any portion of the polymer including a monomer unit, or a block of the polymer, or a sequence of the polymer, etc. "Soft segments" may include a soft phase of the polymer, which is amorphous with a glass transition temperature below the use temperature (e.g., rubbery). "Hard segments" may include a hard phase of the polymer that is crystalline at the use temperature or amorphous with a glass transition temperature above the use temperature (e.g., glassy). The use temperature may include a range of temperatures including room temperature (about 20-25° C.) and body temperature (about 37° C.). Without wishing to be bound to a particular theory, the soft segment may provide for the greatest impact on sorption onto the excipient and the hard segment may impact diffusion across or through the excipient. See e.g., FIG. 1 showing sorption 112 of the API from the reservoir into the excipient 110 and desorption 114 of the API from the excipient into the subject. Any suitable polymer comprising hard and soft segments may be selected by one of ordinary skill in the art, as long as the polymer allows for delivery of a therapeutically effective amount of the API to the subject at a pseudo-zero order rate for the intended period of time of the implant. In one embodiment of the present invention, the selected polymer excipient is hydrophobic.

In one embodiment, the polymer is a thermoplastic elastomer or elastomeric polymer, which encompasses polymers (homopolymers, copolymers, terpolymers, oligomers, and mixtures thereof) having elastomeric properties and containing one or more elastomeric subunits (e.g., an elastomeric soft segment or block). The thermoplastic elastomers may include copolymers (e.g., styrenic block copolymers, polyolefin blends, elastomeric alloys, thermoplastic polyurethanes, thermoplastic copolyester, and thermoplastic polyamides) or a physical mix of polymers (e.g., a plastic and a rubber), which consist of materials with both thermoplastic and elastomeric properties, for example, comprising a weaker dipole or hydrogen bond or crosslinking in one of the phases of the material. The elastomeric polymer may comprise polyurethanes, polyethers, polyamides, polycarbonates, polysilicones, or copolymers thereof. Thus, the polymer may include elastomeric polymers comprising polyurethane-based polymers, polyether-based polymers, polysilicone-based polymers, polycarbonate-based polymers, or combinations thereof. In an exemplary embodiment, the polymer comprises a polyurethane-based polymer or a polyether-block-polyamide polymer.

Suitable hard and soft segments of the polymer may be selected by one of ordinary skill in the art. It will be appreciated by one of ordinary skill in the art that although certain types of polymers are described herein, the hard and soft segments may be derived from monomers, polymers, portions of polymers, etc. In other words, the polymers listed may be changed or modified during polymerization, but those polymers or portions of those polymers in polymerized form constitute the hard and soft segments of the final polymer.

Examples of suitable soft segments include, but are not limited to, those derived from (poly)ethers, (poly)carbonates, (poly)silicones, or the like. For example, the soft segments may be derived from alkylene oxide polymers selected from the group consisting of poly(tetramethylene oxide) (PTMO), polyethylene glycol (PEG), poly(propylene oxide) (PPO), poly(hexamethylene oxide), and combinations thereof. The soft segment may also be derived from polycarbonate soft segments (obtainable from Lubrizol) or silicone soft segments (obtainable from Aortech).

Examples of suitable hard segments include, but are not limited to, those derived from polyurethanes or polyamides. For example, the hard segments may be derived from isocyanates and amides, such as nylons, nylon derivatives (such as nylon 6, nylon 11, nylon 12, etc.), carboxylic acid terminated amide blocks, and the like.

The polymer may be formed by any suitable means or techniques known to one of ordinary skill in the art. For example, the polymer may be formed from monomers, polymer precursors, pre-polymers, polymers, etc. Polymer precursors may include monomeric as well as oligomeric substances capable of being reacted or cured to form polymers. The polymers may be synthesized using any suitable constituents.

In one embodiment of the present invention, the polymer comprises polyurethanes (e.g., comprising a urethane linkage, —RNHCOOR'—). Polyurethanes may include polyether-based polyurethanes, polycarbonate-based polyurethanes, polyamide-based polyurethanes, polysilicone-based polyurethanes, or the like, as discussed in detail above.

Polyurethanes may contain both soft segments and hard segments. The soft segments may be derived from polyols including polyether polyols, polycarbonate-based polyols, and the like. For example, soft segments may be derived from polyether polyols, such as polyalkylene glycols (e.g., polyethylene glycols, polypropylene glycols, polybutylene glycols, polyoxyethylene diols and triols), polyoxypropylene diols and triols, and the like. Soft segments may alternatively be derived from polyols, such as 1,4-butanediol, 1,6-hexanediol, 1,12-dodecanediol, and the like. An elution rate for a composition comprising a polycarbonate soft segment polyurethane is provided in FIG. 12. The soft segment derived from the polyols may be represented by the following formulas or mixtures thereof, for example:

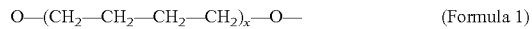  (Formula 1)

  (Formula 2)

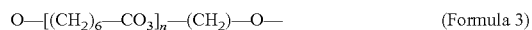  (Formula 3)

The hard segments may be derived from isocyanates, such as aliphatic and cycloaliphatic isocyanates, as well as aromatic isocyanates, such as 1,6-hexamethylene diisocyanate (HDI), 1-isocyanato-3-isocyanatomethyl-3,5,5-trimethyl-cyclohexane (isophorone diisocyanate, IPDI), and 4,4'-diisocyanato dicyclohexylmethane (H12MDI), as well as methylene diphenyl diisocyanate (MDI) and toluene diisocyanate (TDI).

In another embodiment of the present invention, the polymer may comprise a polyether-based polyurethane. For example, the polymer may be an aliphatic polyether-based polyurethane comprising poly(tetramethylene oxide) as the soft segment and polymerized 4,4'-diisocyanato dicyclohexylmethane (H12MDI) and 1,4-butanediol as the hard segment. A suitable polymer includes a polymer from the TECOFLEX® family, an aliphatic block copolymer with a hard segment consisting of polymerized 4,4'-diisocyanato dicyclohexylmethane (H12MDI) and 1,4-butanediol, and a soft segment consisting of the macrodiol poly(tetramethylene oxide).

In another embodiment of the present invention, the polymer comprises polyether-amides (e.g., thermoplastic poly (ether-block-amide)s, e.g., PEBA, PEB, TPE-A, and commercially known as PEBAX® polyether-amides). The hard segment may comprise the polyamide blocks (e.g., carboxylic acid terminated amide blocks, such as dicarboxylic blocks) and the soft segments may comprise the polyether blocks (e.g., a diol, such as polyoxyalkylene glycols). The general structural formula of these block copolymers may be depicted as follows:

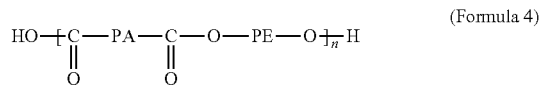

(Formula 4)

where PA represents the hard segment and PE represents the soft segment. The polyamide block may include various amides including nylons (such as nylon 6, nylon 11, nylon 12, etc.). The polyether block may also include various polyethers, such as poly(tetramethylene oxide) (PTMO), polyethylene glycol (PEG), poly(propylene oxide) (PPO), poly(hexamethylene oxide), polyethylene oxide (PEO), and the like. The ratio of polyether to polyamide blocks may vary from 80:20 to 20:80 (PE:PA). As the amount of polyether increases, a more flexible, softer material may result.

In one embodiment, the elastomeric polymer is selected from the group consisting of TECOFLEX® polyurethanes, CARBOTHANE® polyurethanes, PEBAX® polyether-amides, and combinations thereof. For example, the elastomeric polymer may include TECOFLEX® EG-93A polyurethane, TECOFLEX® EG-80A polyurethane, TECOFLEX® EG-85A polyurethane, PEBAX® 2533 polyether-amide, PEBAX® 3533 polyether-amide, CARBOTHANE® PC-3585A polyurethane, and combinations thereof.

The relative content of the soft and hard segments may provide an elution rate within a target range of average daily elution rate for the active pharmaceutical ingredient. The relative content of the soft and hard segments refers to the amount or content of soft segments to hard segments in the polymer. The relative content may also be defined as a ratio of soft segment to hard segments (e.g., at least about 2:1 or at least about 4:1 of soft to hard segments). For example, the soft content may be 50% or more, 60% or more, 70% or more, or 80% or more relative to the hard content. In one embodiment, the relative content is about 70% soft segments and about 30% hard segments or at least about 2.3:1 soft:hard (e.g., PEBAX® 2533 polyether-amide). In another embodiment, the relative content is about 80% soft segments and about 20% hard segments or at least about 4:1 soft:hard (e.g., PEBAX® 3533 polyether-amide).

The ratio of soft to hard segments may vary depending on the desired elution rate. Without wishing to be bound to a particular theory, it is believed that the soft segments may contribute to the sorption of the API into the excipient and/or the hard segment may contribute to the rate of diffusion (e.g., how fast the active diffuses through the excipient). The rate of diffusion through the excipient probably does not matter much, however, once the implant reaches steady state (e.g., a constant or near constant elution rate). Thus, it may be desirable to have a higher ratio of soft segments relative to hard segments (e.g., at least about 2:1, at least about 3:1, or at least about 4:1). The relative content of the soft and hard segments may also be considered directly proportional on the molecular weights of both the soft and hard segments. In other words, for a given ratio, a higher molecular weight polymer for the soft segment results in a higher relative content of soft segments to hard segments.

The molecular weights of each of the soft and hard segments may be selected depending on the specific soft and hard segments selected. In particular, the size (e.g., molecular weight) of the soft segment may impact the elution rate. For example, the soft block (e.g., polyether) molecular weights may range from about 1000-12,000 daltons (daltons may be used interchangeably with g/mol for molecular weight). For the case of PTMO as the soft segment, the molecular weights may range from about 500-3000 daltons. In some cases, a higher molecular weight may be preferred (e.g., about 2000-3000 daltons) in order to elevate elution, as compared to less than about 1000 daltons. For the case of PPO as the soft segment, the molecular weight may range from about 2000-12,0000 daltons, and again a higher molecular weight may be preferred to elevate elution rates. For the case of polyether-block amides, the molecular weight of the polyether block may vary from about 400 to about 3000 daltons and that of the polyamide block may vary from about 500 to about 5000 daltons. Without wishing to be bound to a particular theory, it is believed that by increasing the molecular weight of soft segments in the polymer, the content of hard segments is reduced providing for better dissolution and diffusion of the API through the excipient.

The Shore D hardness or Shore hardness of the polymer segments may also have an impact on the elution rates. In some cases, the Shore hardness may be inversely proportional to the elution rate (e.g., a higher Shore hardness results in a lower elution rate). For example, in the case of polyether-block amides, a Shore hardness of 35 provides a lower elution rate as compared to a Shore hardness of 25. In one embodiment of the present invention, the excipient is substantially or completely non-porous, in that the polymer has a porosity or void percentage less than about 10%, about 5%, or about 1%, for example. In particular, the excipient is substantially non-porous in that there are no physical pores or macropores which would allow for egress of the API from the drug delivery composition. In another embodiment, the excipient is practically insoluble in water, which equates to one gram in >10,000 mL of water. In another embodiment of the present invention, the drug delivery composition does not require erosion or degradation of the excipient in vivo in order to release the API in a therapeutically effective amount. Alternatively, the excipient is not substantially erodible and/or not substantially degradable in vivo for the intended life of the implantable composition (e.g., the API is not released due to erosion or degradation of the material in vivo).

The rate-controlling excipient may comprise a substantially non-porous, elastomeric polymer comprising soft and hard segments selected based on the relative content of soft and hard segments of the polymer to obtain an elution rate within a target range of average daily elution rate for the active pharmaceutical ingredient. A therapeutically effective amount of the API is delivered to the subject at a pseudo-zero order rate within a target range between a maximum and minimum value of a desired average daily elution rate for the active pharmaceutical ingredient. Pseudo-zero order refers to a zero-order, near-zero order, substantially zero order, or controlled or sustained release of the API. The composition may initially release an amount of the API that produces the desired therapeutic effect, and gradually and continually release other amounts of the API to maintain the level of therapeutic effect over the intended duration of treatment (e.g., about one year).

As previously noted, the excipient defines the shape of the reservoir, which may be of any suitable size and shape. In an exemplary embodiment, the excipient is substantially cylindrically shaped. An embodiment of a cylindrically shaped excipient is depicted, for example, in FIG. 2. The reservoir may be of any suitable size depending on the active and location of delivery, e.g., a ratio of about 1:1.5 to 1:15, for example about 1:5 or about 1:10 diameter to length.

The wall thickness of the excipient may also be selected to provide for the desired elution rate. The wall thickness may be inversely proportional to elution rate. Thus, a larger wall thickness may result in a lower elution rate. The excipient may form a wall having an average thickness of about 0.05 to about 0.5 mm, or about 0.1 mm to about 0.3 mm (e.g., about 0.1 mm, about 0.2 mm, or about 0.3 mm).

The polymers may be processed using any suitable techniques, such as extrusion, injection molding, compression molding, spin-casting. In one embodiment, a method of making an implantable drug delivery composition includes: (a) selecting a substantially non-porous elastomeric polymer comprising soft and hard segments based on the relative content and molecular weights of the soft and hard segments of the polymer to provide an elution rate within a target range of average daily elution rate for tizanidine; (b) forming a hollow tube from the elastomeric polymer (see e.g., FIG. 2); (c) selecting and formulating the tizanidine free base and at least one sorption enhancer in order to produce an elution rate at a therapeutically effective amount of the tizanidineat pseudo-zero order for a period of time of at least one month, wherein the amount of sorption enhancer is directly proportional to the average daily elution rate; (d) loading at least one discrete solid dosage form comprising the tizanidine free base and the at least one sorption enhancer into the tube; and (e) sealing both ends of the tube to form a sealed cylindrical reservoir-based drug delivery composition. The tube may be sealed using any suitable means or techniques known in the art. For example, the ends may be plugged, filled with additional polymers, heat sealed, or the like. The tubes should be permanently sealed such that the discrete solid dosage forms may not be removed. Also, the ends should be suitably sealed such that there are no holes or openings that would allow egress of the active once implanted.

Sorption Enhancer(s) and the Discrete Dosage Form

According to an aspect of the present invention, the at least one discrete solid dosage form, within the reservoir, may also comprise at least one sorption enhancer in an amount effective to modulate the average daily elution rate of the active pharmaceutical ingredient to provide for release of the active pharmaceutical ingredient at pseudo-zero order within the target range at the therapeutically effective amount for a period of time of at least one month. As used herein, the terms "modulate" or "modulation" may be used to describe a change in the activity of the drug delivery composition. This may equate to a change in elution rate (e.g., an increase or a decrease in a given elution rate or range).

Sorption enhancers may include compounds which improve the release of the API from the drug delivery composition. Without wishing to be bound to a particular theory, the sorption enhancers may improve release of the API from the drug delivery composition by drawing water or other fluids into the reservoir from the subject, disintegrating or breaking apart the discrete solid dosage form(s), and/or allowing the API to come into contact or remain in contact the inner walls of the excipient. Such a mechanism may be depicted, for example, in FIG. 1.

The amount of the sorption enhancer is not particularly limited, but, when present, is preferably on the order of about 1-25 wt % of the solid dosage form, more preferably about 5-20 wt % of the solid dosage form, and more preferably about 10 wt %. The amount of sorption enhancer may be directly proportional to the elution rate. In other words, a higher weight percent of sorption enhancer in the composition may result in a higher average elution rate than a smaller weight percentage. Thus, it may be preferable to include a higher weight percent of sorption enhancer to give a higher elution rate (e.g., about 8-25 wt % or about 10-20 wt %).

Any suitable sorption enhancer(s) may be selected by one of ordinary skill in the art. Particularly suitable sorption enhancer(s) may include, for example, negatively-charged polymers, such as croscarmellose sodium, sodium carboxymethyl starch, sodium starch glycolate, sodium acrylic acid derivatives (e.g., sodium polyacrylate), cross-linked polyacrylic acid (e.g., CARBOPOL®), chondroitin sulfate, poly-glutamic acid, poly-aspartic acid, sodium carboxymethyl cellulose, neutral polymers, such as polyethylene glycol, polyethylene oxide, polyvinylpyrrolidone, and combinations thereof. In an exemplary embodiment, the sorption enhancer is croscarmellose sodium. The amount of the sorption enhancer is not particularly limited, but, when present, is preferably on the order of about 1-25 wt % of the solid dosage form, about 2-20 wt % of the solid dosage form, about 2-12 wt % of the solid dosage form, about 5-10 wt % of the solid dosage form (e.g., about 5 wt % or about 10 wt % of the solid dosage form). The selection of the specific sorption enhancer may have an impact on the elution rate.

In one embodiment of the present invention, the at least one discrete solid dosage form comprises: 75-97 wt % tizanidine free base based on the total weight of the at least one discrete solid dosage form; 1-25 wt % of at least one sorption enhancer based on the total weight of the at least one discrete solid dosage form; and 0-5 wt % lubricant based on the total weight of the at least one discrete solid dosage form. For example, 85-95 wt % (e.g., about 88 wt %) tizanidine free base based on the total weight of the at least one discrete solid dosage form; 5-20 wt % (e.g., about 10 wt %) of at least one sorption enhancer (e.g., croscarmellose sodium) based on the total weight of the at least one discrete solid dosage form; and 0-5 wt % (e.g., about 2%) lubricant (e.g., stearic acid) based on the total weight of the at least one discrete solid dosage form. Preferably, each component of the drug delivery composition is provided in an amount effective for the treatment of the disease or condition being treated.

As previously discussed, the therapeutically effective amount of the API may be delivered to the subject at a target range of average daily elution rate for the API. The target elution rate (mg/day) is based on the oral dose rate multiplied by the fractional oral bioavailability. The elution rate may be an average rate, e.g., based on the mean average for a given period of time, such as a day (i.e., average daily elution rate).

The average daily elution rate of the active pharmaceutical ingredient may vary in direct proportion to the amount of sorption enhancer in the drug delivery composition (e.g., more sorption enhancer may provide for a higher average daily elution rate).

As previously discussed, the minimum value(s) for the average daily elution rate may be correlated to the trough value for an oral dosage version of the API (e.g., based on the blood/plasma concentrations for oral formulations). Similarly, the maximum value(s) may be correlated to the peak value for an oral dosage version of the API (e.g., the maximum blood/plasma concentration when an oral dosage is first administered or a pharmaceutically toxic amount). In other words, the target range is between maximum and minimum elution rates, respectively, which may be determined based on blood/plasma concentrations for equivalent oral dosage forms containing the same active. The number and shape of the discrete dosage form(s) may be optimized to provide for the desired elution rates. For example, the discrete solid dosage forms may be of suitable shape to not fill the entire cavity of the reservoir. In one embodiment, the at least one discrete dosage form is cylindrical in shape. In another embodiment, the at least one discrete dosage form is substantially spherical in shape in that the solid dosage forms are spherical or nearly spherical. For example, the shape of the dosage form may not deviate from a perfect sphere by more than about 10%. In another embodiment, the at least one discrete dosage form is substantially cylindrical.

Without wishing to be bound by any theory, it is believed that the surface area of the at least one discrete dosage forms contributes to the elution rate. In one embodiment, the total surface area of the at least one discrete dosage forms is directly proportional to elution rate. Thus, the number of discrete dosage forms may be selected to provide a given elution rate, wherein an increased number of dosage forms provides an increased total surface area. The discrete solid dosage forms may comprise more than one pellet (e.g., 2-9 pellets). In other words, a higher number of dosage forms may result in a higher average elution rate than a smaller number of dosage forms. Thus, it may be preferable to include more discrete solid dosage forms to give a higher elution rate (e.g., 7-9 pellets). In a further embodiment, the overall surface area of the pellets used in the implantable drug delivery composition can be increased, for example by changing the shape of the pellets, increasing their surface convolution, etc.

Drug Delivery Compositions, Subcutaneous Delivery Systems, and Kits

As previously noted, the drug delivery composition is long lasting, and the tizanidine may be delivered to the subject at a pseudo-zero order rate for an extended period of time (e.g., at least about one month (about one month or greater), at least about three months (about three months or greater), at least about six months (about six months or greater), at least about one year (about one year or greater), at least about two years (about two years or greater), at least about 30 months (about 30 months or greater), or any period of time within those ranges).

According to one embodiment of the present invention, a subcutaneous delivery system for releasing tizanidine at a pseudo-zero order comprises an elastomeric reservoir implant comprising a rate-controlling excipient defining a reservoir. The rate-controlling excipient comprises a substantially non-porous elastomeric polymer having a relative content of hard segments and soft segments to provide an elution rate within a target range of average daily elution rate for the tizanidine. The reservoir containing at least one discrete solid dosage form comprising tizanidine free base and an effective amount of at least one sorption enhancer to modulate the elution rate of the tizanidine for release of a therapeutically effective amount of the tizanidine within the target range at pseudo-zero order for a period of time of at least one month. The amount of sorption enhancer may be directly proportional to the average daily elution rate.

The drug delivery composition may be implanted into the subject in any suitable area of the subject using any suitable means and techniques known to one of ordinary skill in the art. For example, the composition may be implanted subcutaneously, e.g., at the back of the upper arm or in the upper back (e.g., scapular region), by directly depositing in or underneath the skin, a subcutaneous fat layer, or intramuscularly.

According to another embodiment of the present invention, a kit for subcutaneously placing a drug delivery composition includes a reservoir-based drug delivery composition comprising a rate-controlling excipient defining a reservoir containing at least one discrete solid dosage form and an implanter for inserting the reservoir-based drug delivery composition beneath the skin, and optionally instructions for implantation and explantation of the drug delivery composition. The rate-controlling excipient comprises a substantially non-porous, elastomeric polymer comprising soft and hard segments and the relative content of soft and hard segments of the polymer are selected to obtain an elution rate within a target range of average daily elution rate for the tizanidine. The at least one discrete solid dosage form preferably comprises tizanidine free base and at least one sorption enhancer in an amount effective to modulate the elution rate of the tizanidine to provide for release of the tizanidine at pseudo-zero order within the target range at the therapeutically effective amount for a period of time of at least one month, and the amount of sorption enhancer may be directly proportional to the average daily elution rate.

The drug delivery composition may be delivered subcutaneously using any suitable equipment or techniques, e.g., an implanter known to one ordinary skill in the art. The kits may comprise the drug delivery composition pre-loaded into the implanter or the drug delivery composition may be loaded by the doctor or other user. The implanter may be an implantation device, such as a syringe, cannula, trocar or catheter, that may be inserted into an incision made at the delivery site of the subject. Suitable implantation devices and implantation methods include the trocar and methods disclosed in U.S. Pat. No. 7,214,206 and U.S. Pat. No. 7,510,549, the disclosures of which are herein incorporated by reference in their entirety, for all purposes. Other suitable methods for implanting or otherwise positioning the compositions into the body, e.g., by a doctor, are well known in the art. Removal and/or replacement may also be accomplished using suitable tools and methods known in the art. Kits may also comprise other equipment well known in the art, such as scalpels, clamps, suturing tools, hydration fluid, and the like.

Embodiments of Kits and Methods of Use Thereof

As used herein, the terms "proximal" and "distal" refer respectively to the directions closer to and further from the surgeon implanting the drug-eluting implant. For purposes of clarity, the distal portion of the insertion instrument is inserted into a subject and the proximal portion of the instrument remains outside the subject. For frame of reference in the figures, arrows marked "P" refer generally to the proximal direction and arrows marked "D" refer generally to the distal direction relative to the orientation of the items depicted in the figures.

Figure 8:
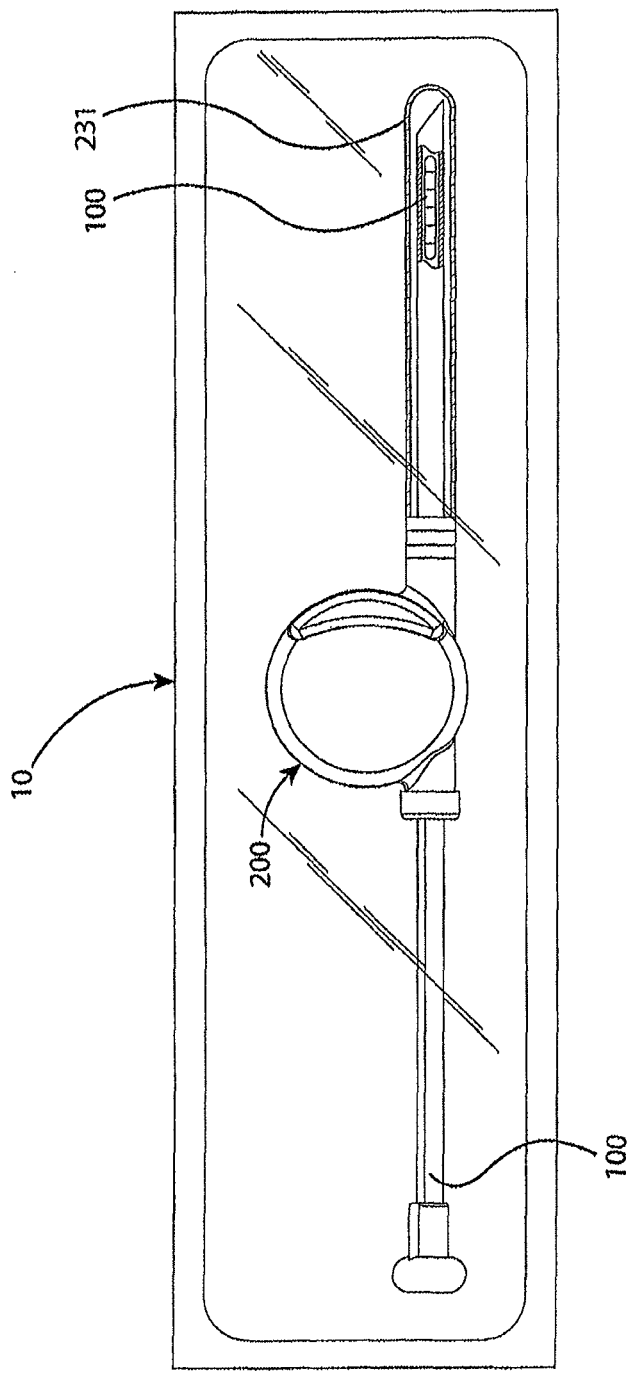
FIG. 8 is a perspective view of a kit for subcutaneously placing a drug-eluting implant in a subject according to embodiments of the invention.
Figure 15:
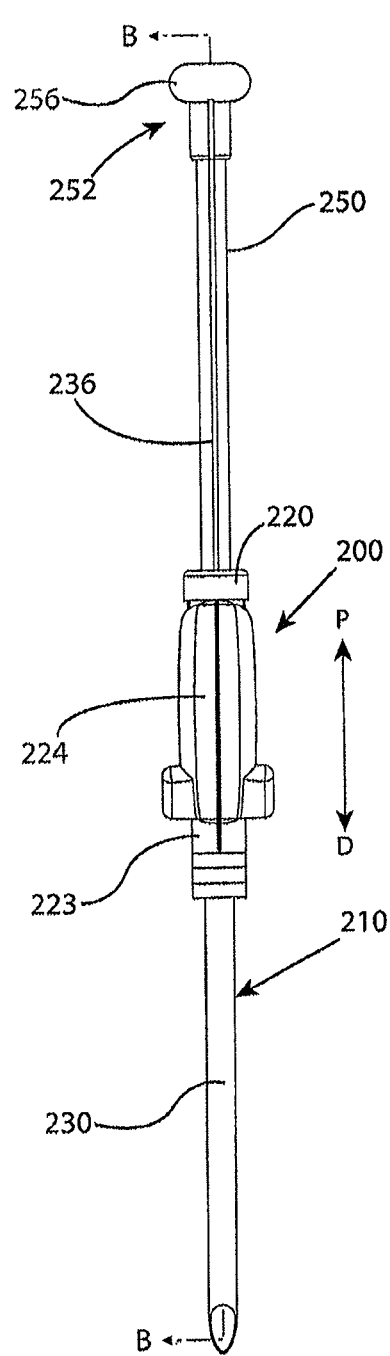
FIG. 15 is a top plan view of the insertion instrument of FIG. 8.
Figure 16:
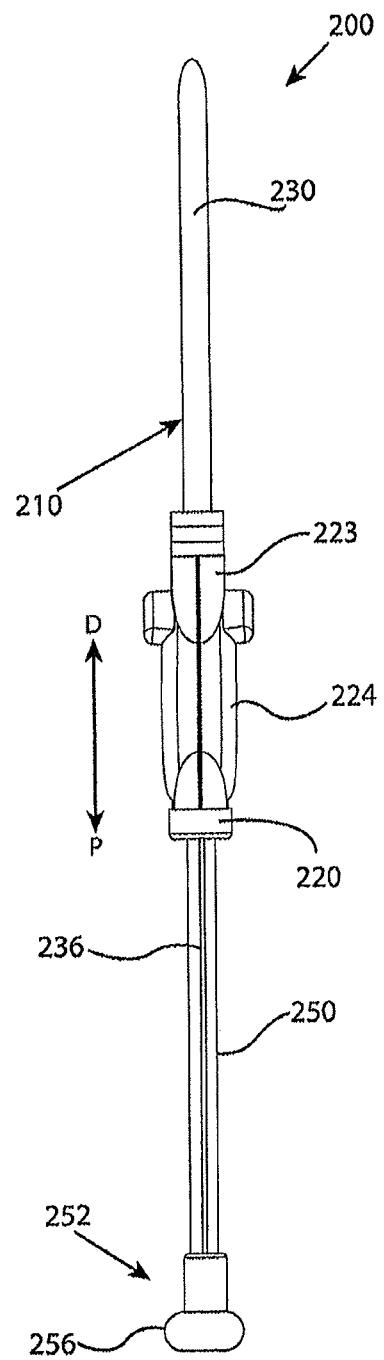
FIG. 16 is a bottom plan view of the insertion instrument of FIG. 8.

Referring to FIG. 8, a kit 10 for subcutaneously placing a drug-eluting implant in a subject is shown in accordance with one exemplary embodiment of the invention. Kit 10 includes a drug-eluting implant 100 and an insertion instrument 200 for subcutaneously placing the drug-eluting implant in a subject. Insertion instrument 200 is packaged with implant 100 pre-loaded into the insertion instrument 200. Although insertion instrument 200 is shown with a single drug-eluting implant 100, the instrument may be pre-loaded with two or more drug-eluting implants to be implanted into a subject. In addition, one or more drug-eluting implants 100 may be provided in kit 10 that are packaged separately from insertion instrument 200.

Referring to FIGS. 9-17, insertion instrument 200 includes a cannula 210 having a hollow shaft 230 where the cannula 210 connects to a front hub portion 223 of a handle portion 224 of the insertion instrument 200. The cannula and hence the hollow shaft 230 has a longitudinal axis 240 and forms an interior bore or lumen 232 that extends through the hollow shaft. The cannula 210 has a sharp distal end 234 that may be covered by a protective sheath 231, shown in FIG. 9, when insertion instrument 200 is not in use. Insertion instrument 200 also includes a stop rod 250 capable of extending through (i) a rear hub portion 220 of the handle portion 224, (ii) the handle portion 224, (iii) the front hub portion 223 of the handle portion 224, and (iv) into hollow shaft 230. Cannula 210 is slidably displaceable over stop rod 250, as will be described in more detail.

In accordance with embodiments of the invention, the handle portion 224 may be formed with a number of different constructs. For example, handle portion 224 may be constructed from two injection molded portions 220a and 220b. Portions 220a and 220b may connect to one another with, for example, a plurality of pins (not shown) that mate with a corresponding plurality of sockets 228 (shown in FIG. 17). When portions 220a and 220b are connected with one another, they collectively form the rear hub portion 220 and the front hub portion 223 of the handle portion 224, and the handle portion 224. As will be readily apparent to those skilled in the art, other constructions are possible for handle portion 224. Front hub portion 223 is adapted to receive the cannula 210 and stop rod 250 therein. Handle portion 224 is offset to one side of longitudinal axis 240 of hollow shaft 230, forming a lateral extension that can be gripped by the user. A pair of flanges 221 project outwardly from handle portion 224 for engagement with a user's fingers.

Distal end 234 of hollow passage 230 provides a passageway into lumen 232. Lumen 232 is adapted to receive and store drug-eluting implant 100 inside hollow shaft 230. Drug-eluting implant 100 can be loaded into lumen 232 by inserting the implant through open distal end 234 and into hollow shaft 230. In this arrangement, drug-eluting implant 100 can be pre-loaded into insertion instrument 200 by the manufacturer after the instrument 200 is assembled. Alternatively, drug-eluting implant 100 can be loaded into insertion instrument 200 by the user.

Figure 17:
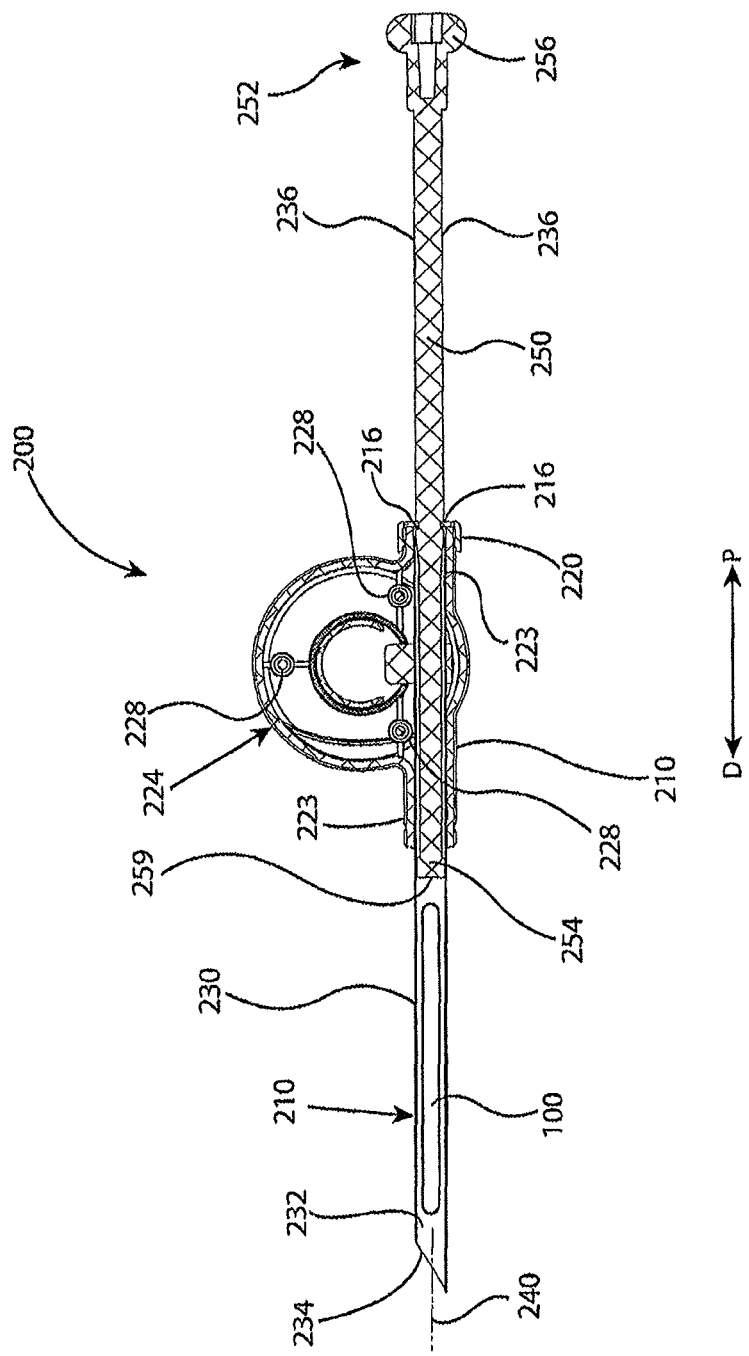
FIG. 17 is a cross-sectional view about section line B-B in FIGS. 10 and 15 of the insertion instrument of FIG. 8.

Referring to FIG. 17, insertion instrument 200 is shown in a ready-to-use condition, with drug-eluting implant 100 pre-loaded into hollow shaft 230 of the cannula 210. Stop rod 250 includes a proximal end 252 and a distal end 254. Proximal end 252 of stop rod 250 includes a knob or handle portion 256. Distal end 254 of stop rod 250 includes an abutment face 259. Abutment face 259 is disposed within hollow shaft 230 in close proximity to drug-eluting implant 100.

Cannula 210 is slidably displaceable over stop rod 250, as noted above. Insertion instrument 200 has two settings, one which allows axial displacement of the cannula 210 over stop rod 250, and one that prevents axial displacement. The settings are controlled by the relative orientation of stop rod 250 with respect to cannula 210. Stop rod 250 is axially rotatable relative to longitudinal axis 240 of hollow shaft 230 between an unlocked orientation and a locked orientation. In the unlocked orientation, cannula 210, front hub 223 and rear hub 220 are permitted to slide over stop rod 250. In the locked orientation, cannula 210, front hub 223 and rear hub 220 are prevented from sliding over stop rod 250.

Stop rod 250 includes a first locking feature defined by two longitudinal grooves 236 as best seen in FIG. 9A. Grooves 236 extend along a portion of the length of stop rod 250. Handle portion 224 includes a second locking feature defined by a pair of projections 216 located on rear hub 220 as best seen in FIG. 17. Each projection 216 extends radially inwardly toward horizontal axis 240 of the hollow shaft 230. When stop rod 250 is rotated into the locked orientation, grooves 236 are not in radial alignment with projections 216. As such, projections 216 engage stop rod 250, preventing cannula 210 from sliding over the stop rod toward proximal end 252 of the stop rod. When stop rod 250 is rotated to the unlocked orientation, grooves 236 are positioned in radial alignment with projections 216. Each groove 236 is sized to receive one of the projections 216. Therefore, in the unlocked position, each projection 216 is received within a groove 236 thereby permitting the cannula 210 to slide over stop rod 250 toward proximal end 252 of the stop rod 250. Stop rod 250 may include spaced markings thereon to indicate the distance that the cannula 210 has been moved proximally with respect to the proximal end 252 of the stop rod 250.

Insertion instrument 200 is packaged in the kit 10 with the drug-eluting implant 100 pre-loaded into the cannula 210. In alternative embodiments, the kit may be provided with an insertion instrument 200 and a drug-eluting implant 100, with the implant packaged separately from the instrument (i.e. the instrument is contained in one package in the kit, and the implant is contained in a separate package in the kit outside of the package containing the instrument). This packaging option allows a user to remove the drug-eluting implant from its packaging, inspect the implant, and load the implant into the instrument immediately before inserting the implant into the patient. This option also provides the user with the flexibility to substitute the implant provided in the kit with another implant that may be more suitable. Separate packaging may be used with kits that contain multiple implants having different properties. In such kits, the different implants may be individually packaged, and the user may select and open the appropriate implant, and load that implant into the instrument.

Kits in accordance with the invention may contain one or more implants that differ from one another in terms of the drug composition they contain, or other characteristic. For example, kit 10 is provided with a single drug-eluting implant 100. Implant 100 consists of a polymeric rate-controlling excipient, the excipient defining a reservoir containing at least one discrete solid dosage form. Other kit embodiments may be provided with two or more implants consisting of polymeric rate-controlling excipients. Although the figures schematically show a single implant 100 pre-loaded in insertion instrument 200, other embodiments in accordance with the invention may feature insertion instruments pre-loaded with two or more implants 100. Kits in accordance with embodiments of the invention may be provided with an insertion instrument pre-loaded with one or more implants, and one or more separately packaged implants that are not pre-loaded in the insertion instrument. Any number, type or combination of implants and instruments, whether packaged together or separately, may be provided in kits in accordance with embodiments of the invention. Thus, multiple implants having different therapeutic effects may be implanted in a single delivery procedure.

Figure 18:
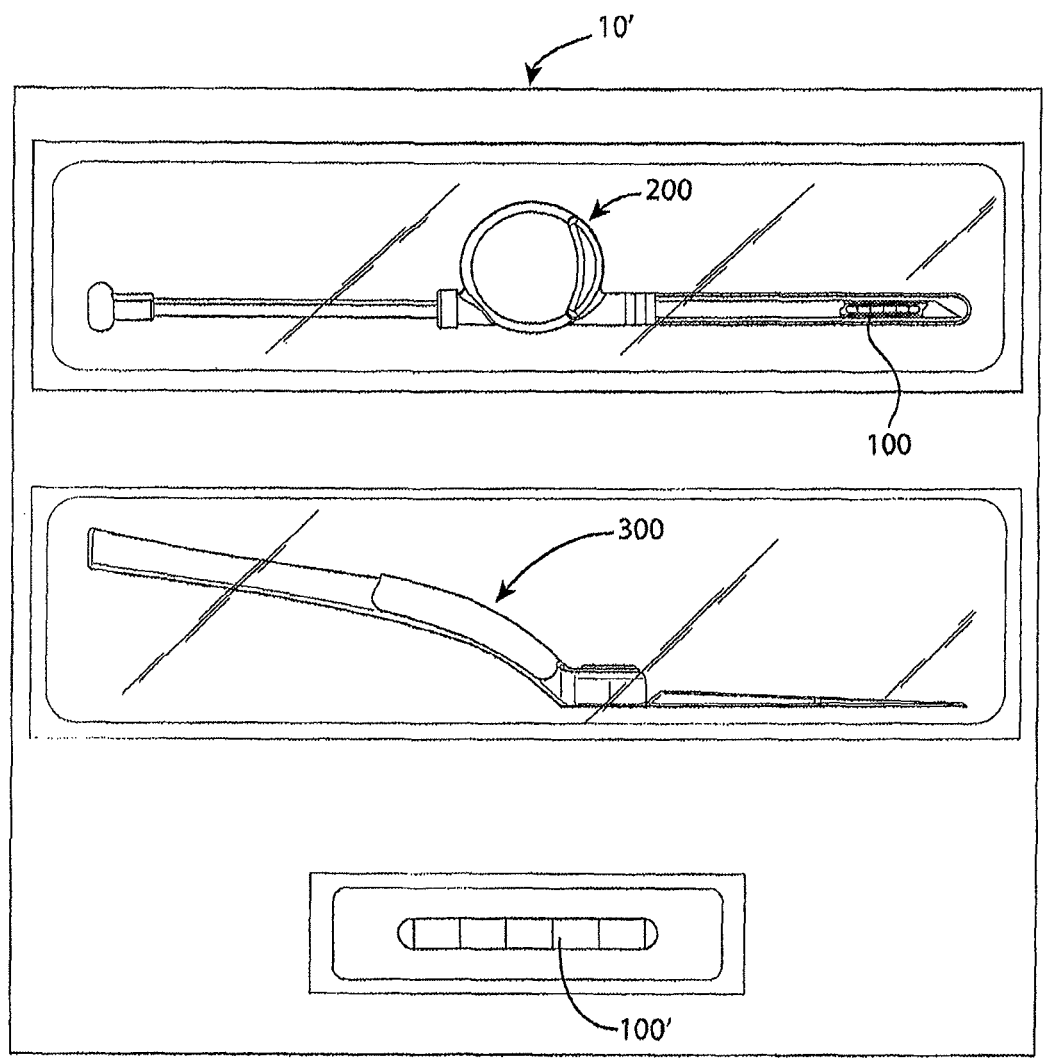
FIG. 18 is a perspective view of another kit for subcutaneously placing a drug-eluting implant in a subject, according to another aspect of the invention.
Figure 21:
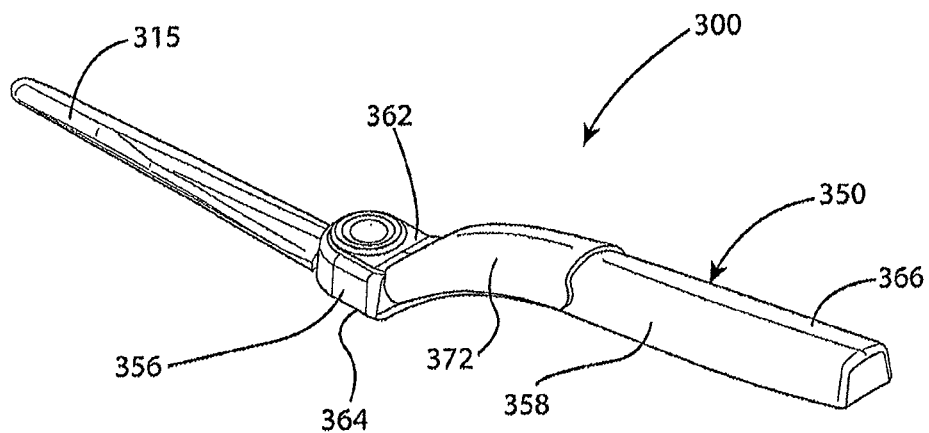
FIG. 21 is a perspective view of the tunneling instrument of FIG. 18.

It is desirable in some instances to prepare a subcutaneous cavity beneath the cutis, prior to inserting insertion instrument 200 into the subject. The subcutaneous cavity provides a pocket that is large enough to receive the full length of the hollow shaft of the cannula, making it easier to deposit the implant in the proper location. For this reason, kits in accordance with embodiments of the invention may optionally include a separate instrument for preparing a subcutaneous cavity in a subject. Referring to FIG. 18, an alternate kit 10' in accordance with embodiments of the invention is shown. Kit 10' includes the same insertion instrument 200 pre-loaded with a drug-eluting implant 100 as shown in prior figures. Kit 10' also includes a second instrument, referred to as a tunneling instrument 300, for preparing a subcutaneous cavity in a subject. In addition, kit 10' includes another drug-eluting implant 100' that is packaged separately from the instruments.

Figure 22:
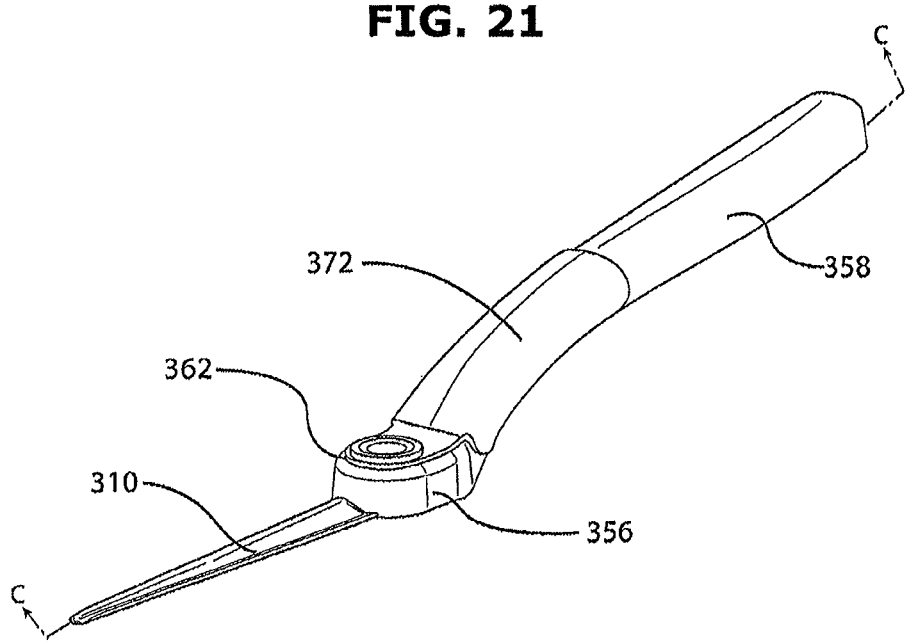
FIG. 22 is another perspective view of the tunneling instrument of FIG. 18.
Figures 23, 24:
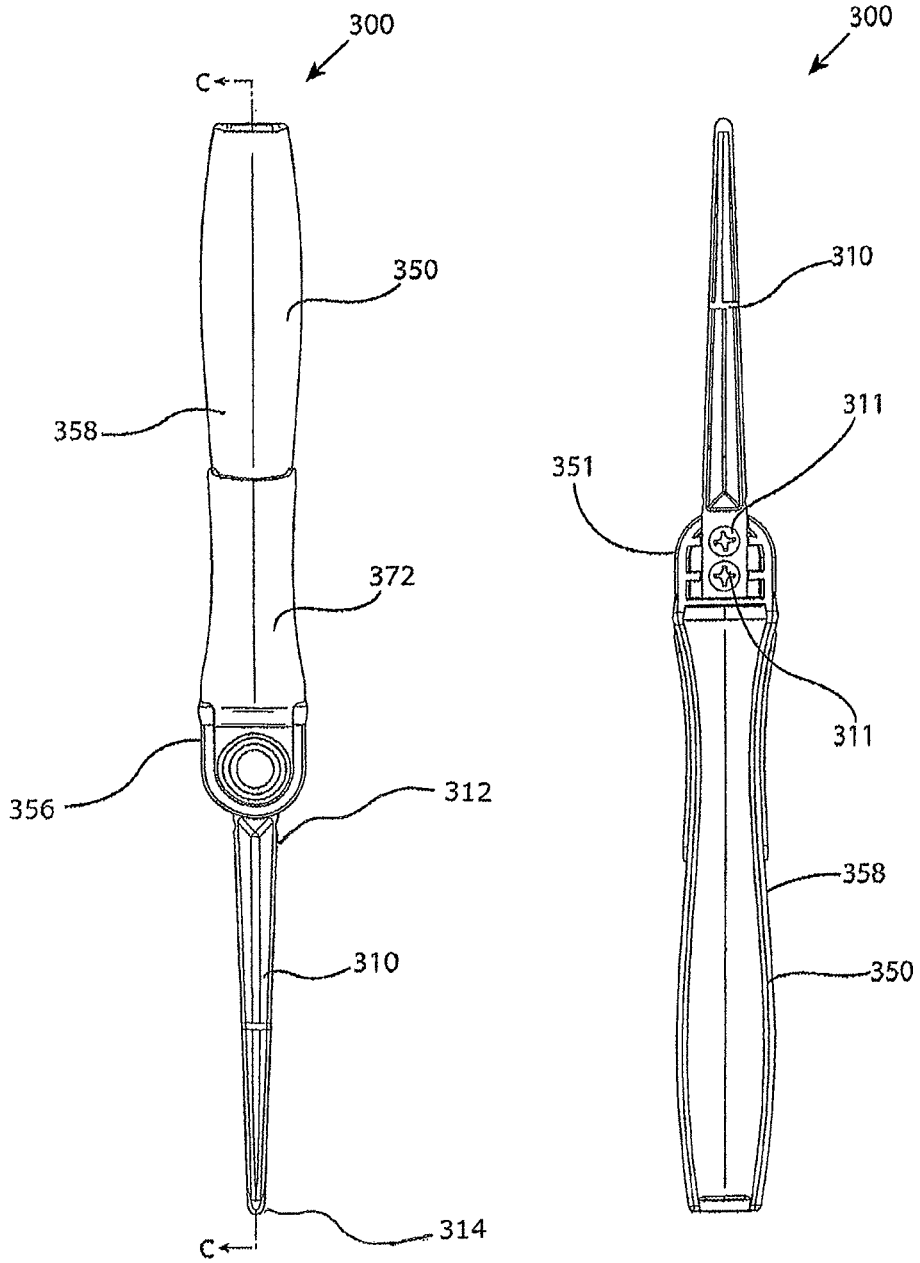
FIG. 23 is a top plan view of the tunneling instrument of FIG. 18.
FIG. 24 is a bottom view of the tunneling instrument of FIG. 18.
Figure 25:
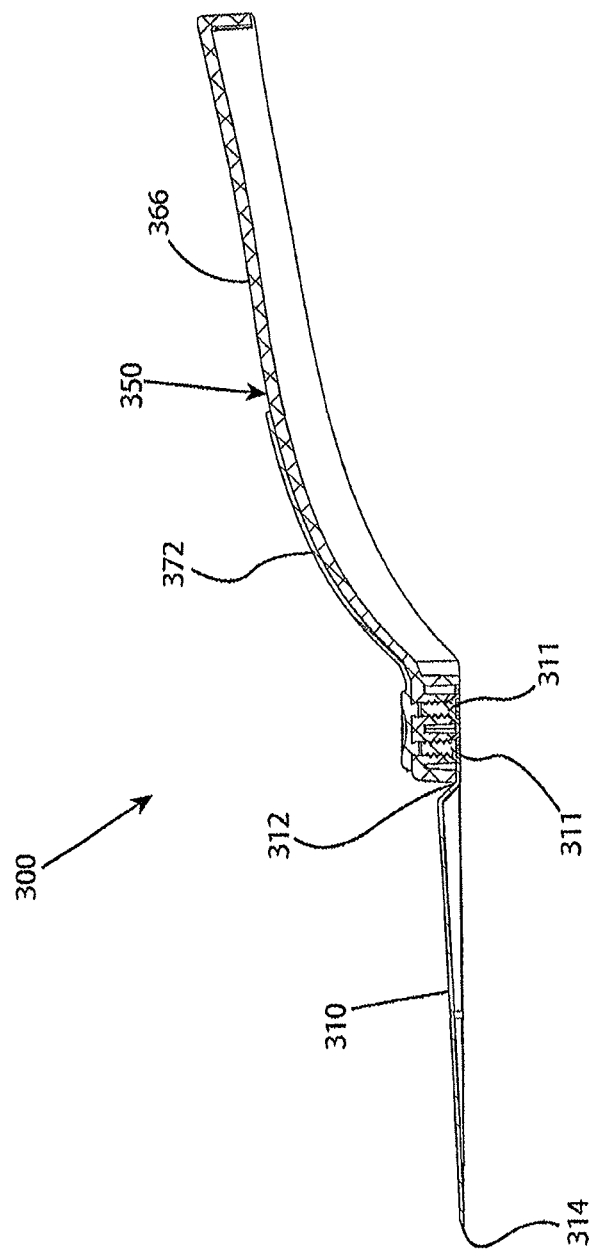
FIG. 25 is a cross-sectional view about section line C-C in FIGS. 22 and 23 of the tunneling instrument of FIG. 18.
Figure 26:
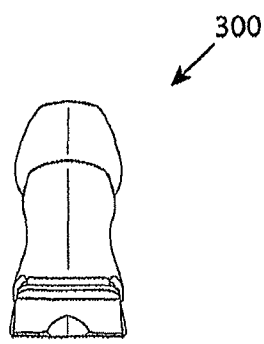
FIG. 26 is a distal end view of the tunneling instrument of FIG. 18.
Figure 27:
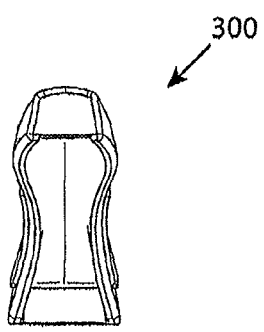
FIG. 27 is a proximal end view of the tunneling instrument of FIG. 18.

Referring to FIGS. 19-27, tunneling instrument 300 has an elongated profile characterized by a horizontal axis H that is parallel to an insertion direction I, and a vertical axis V that is normal to the horizontal axis. Tunneling instrument 300 includes a blade 310 and a handle 350 attached to the blade. Blade 310 has a proximal end 312 and a distal end 314. Handle 350 also has a proximal end 352 and a distal end 354. In the present embodiment, distal end 354 of handle 350 is attached to proximal end 312 of blade 310 by a pair of screws 311. As will be readily apparent to those skilled in the art, blade 310 may be attached to handle 350 by any other means known in the art. When blade 310 is viewed from a side, as shown in FIG. 19, the vertical height or dimension of the blade 310 with respect to vertical axis V gradually increases from distal end 314 toward the proximal end 312. Blade 310 includes a superior surface 316 and an inferior surface 318 opposite the superior surface. Inferior surface 318 extends between the proximal and distal ends 312, 314 of blade 310 and includes a substantially flat portion 322 that extends parallel to horizontal axis H. Superior surface 316 of blade 310 forms an inclined surface 324. Inclined surface 324 extends at an acute angle θ (as best seen in FIG. 20) with respect to flat portion 322. Referring to FIG. 23, blade 310 has a tapered profile with a maximum width at proximal end 312. The width of blade 310 tapers to a minimum width at the distal end 314. Each side of blade 310 follows a gradual curve. Blade 310 may be covered by a protective sheath 315, as shown in FIG. 22, when tunneling instrument 300 is not in use.

Handle 350 includes a base portion 356 and an elongated gripping portion 358 extending from the base portion. Base portion 356 has a superior surface 362 and an inferior surface 364 opposite the superior surface. Inferior surface 364 extends substantially coplanar with flat portion 322 of blade 310 to form a substantially continuous surface between the blade 310 and base portion 356. Gripping portion 358 extends upwardly from base portion 356 with respect to vertical axis V, and features a superior surface 366 and an inferior surface 368. An overmolded grip 372 extends over superior surface 366 of gripping portion 358 and superior surface 362 of base portion 362. Overmolded grip 372 may be formed of rubber or other material that provides a soft cushioned area to grip the instrument.

A method for subcutaneously placing a drug-eluting implant in a subject in accordance with embodiments of the invention will now be described with reference to the instruments in kit 10'. In this example, the method is used to subcutaneously place the implant in the arm of a human subject. The method begins by positioning the patient so that the surgeon has access to the location into which the implant is to be placed. For example, the patient may be positioned lying down on his or her back, with one arm flexed and turned to give the surgeon access to the inner aspect of the upper arm. The insertion site is then located on the upper arm. One possible insertion site is located approximately halfway between the patient's shoulder and elbow, and in the crease between the bicep and triceps. Once the insertion site is selected, the area around the site is swabbed and a local anesthetic is administered. Using a sterile scalpel, the surgeon makes an incision at the insertion site in a direction transverse to the long axis of the upper arm. The length of the incision should be as short as possible, but long enough to allow insertion of blade 310 of tunneling instrument 300 into the incision and under the skin. In alternate embodiments, the drug-eluting implant may be placed without the aid of a tunneling instrument. In such cases, the length of the incision should be as short as possible, but long enough to allow insertion of the cannula 210 of the insertion instrument 200 into the incision and under the skin.

For cases when a tunneling instrument 300 is used, the tunneling instrument 300 is removed from its packaging (if not already done) and placed in proximity to the incision, with flat portion 322 of blade 310 resting on or positioned just above the skin, and distal end 314 of the blade aligned with the incision. Inferior surface 364 of base portion 356 of handle 350 should also be resting on or positioned just above the skin, so that flat portion 322 of blade 310 is substantially parallel to the long axis of the patient's arm. Distal end 314 of blade 310 is then inserted through the incision and advanced into the patient's arm in a direction substantially parallel to the long axis of the arm, with the blade advancing immediately beneath the cutis and into the subcutaneous tissue. As blade 310 is advanced into the arm, the portion of the blade that enters the arm becomes gradually wider and wider in the horizontal and vertical directions due to the geometry of the blade 310 discussed above to expand the cavity created by the blade, forming a pocket or tunnel by blunt dissection. During insertion, the surgeon preferably maintains the insertion path just beneath the cutis and visibly raises the skin with blade 310 until a subcutaneous tunnel of sufficient length and width is created. Blade 310 is then removed from the patient's arm. For single-use kits, tunneling instrument 300 may be discarded.

Insertion instrument 200 is then removed from its packaging (if not already done). As noted above, insertion instrument 200 is packaged in kit 10' with drug-eluting implant 100 pre-loaded into cannula 210. Insertion instrument 200 is preferably packaged with stop rod 250 withdrawn from handle portion 224 and in the locked position as shown in FIG. 8. Prior to use, the surgeon may wish to check that insertion instrument 200 is set with stop rod 250 rotated to the locked position, so as to prevent cannula 210 from being inadvertently advanced over the stop rod 250. The surgeon can determine if stop rod 250 is locked in a number of ways. For example, the surgeon can try sliding the cannula 210 over stop rod 250 to see if the stop rod is locked or unlocked. In addition, or as an alternative, the surgeon can check visible markings on insertion instrument 200 to determine whether stop rod 250 is locked or unlocked. In the illustrated example, rear hub portion 220 has a first indicia 222 in the form of a small horizontal line (as best seen in FIGS. 13 and 14). Stop rod 250 has a second indicia 251 and a third indicia 253 in the form of two horizontal lines that are radially offset from one another on the perimeter of the stop rod (as best seen in FIG.

13). Stop rod 250 is rotatable relative to hub 220 to a first orientation that aligns the second indicia 251 with the first indicia 222. This first orientation corresponds to the locked position. Stop rod 250 is also rotatable relative to the hub 220 to a second orientation that aligns the third indicia 253 with the first indicia 222. This second orientation corresponds to the unlocked position. In preferred embodiments, the instrument includes a mechanism that provides tactile feedback to the surgeon when the stop rod 250 is rotated to the locked and unlocked positions. For example, the instrument may include an internal spring latch that engages a detent inside the hub to make an audible click after the stop rod is rotated to the locked position and/or unlocked position. The second and third indicia may also be color coded (e.g. green and red lines) to suggest which orientation is the unlocked position and which orientation is the locked position.

Once the locked position is confirmed, distal end 234 of cannula 210 is inserted into the incision and advanced into the subcutaneous tissue. Cannula 210 is advanced into the tunnel until a distal end 229 of hub 220 reaches the incision. At this stage, the hollow shaft 230 and hence, the implant 100, is positioned in the tunnel. Stop rod 250 is then rotated to the unlocked position in preparation for withdrawing cannula 210 from the incision. The unlocked position can be confirmed by an audible click, or by visual reference using the first indicia 222 and third indicia 253. The surgeon applies a gentle downward pressure on top of stop rod 250, preferably at or near proximal end 252, so as to fix the position of the stop rod relative to the patient's arm. Once stop rod 250 is fixed, the surgeon holds the stop rod 250 in the fixed position with one hand, and grasps the handle portion 224 of the insertion instrument 200 with the other hand. The surgeon then applies a pulling force on handle portion 224 in a direction away from the incision to withdraw cannula 210 out of the incision. This may be performed in a single rapid motion to withdraw cannula 210 from the tunnel while leaving implant 100 in place in the tunnel. Depending on the length of implant 100 relative to the length of cannula 210 and other factors, the implant may be completely released from the hollow shaft 230 when the cannula 210 is partially removed from the incision (i.e. when a portion of the cannula 210 is withdrawn from the tunnel, while the remaining portion of the cannula 210 still remains in the tunnel). In other scenarios, implant 100 may be completely released from hollow shaft 230 only after the entire cannula 210 is completely removed from the incision (i.e. no portion of the cannula 210 remains in the tunnel).

Depending on factors such as friction, implant 100 may travel a small distance with cannula 210 as the cannula is withdrawn from the tunnel. In the event that implant 100 travels with cannula 210, the implant may travel far enough to contact abutment face 259 of stop rod 250. Abutment face 259 remains fixed inside the tunnel as cannula 210 is withdrawn, preventing the implant from being pulled out of the tunnel as the cannula 210 is withdrawn and removed from the incision.

In another embodiment, the implant 100 may be delivered as follows. Once the locked position is confirmed, distal end 234 of cannula 210 is inserted into the incision and advanced into the subcutaneous tissue. Cannula 210 is advanced into the tunnel until the distal end 234 of the cannula 210 is at the desired location of implant delivery in the tunnel. At this stage, the stop rod 250 is then rotated to the unlocked position in preparation for advancing the implant 100 toward the distal end 234 of the cannula 210. Similar to the previous embodiment, the unlocked position can be confirmed by an audible click, or by visual reference using the first indicia 222 and third indicia 253. The surgeon next pushes the stop rod 250 distally thereby advancing the implant 100 in the hollow shaft 230 toward the distal end 234 of the cannula 210. Once the implant is at the distal end 234, the surgeon then applies a gentle downward pressure on top of stop rod 250, preferably at or near proximal end 252, so as to fix the position of the stop rod relative to the patient's arm. Once stop rod 250 is fixed, the surgeon holds the stop rod 250 in the fixed position with one hand, and grasps the handle portion 224 of the insertion instrument 200 with the other hand. The surgeon then applies a pulling force on handle portion 224 in a direction away from the incision to withdraw cannula 210 out of the incision. Moving the handle portion 224 and hence, the cannula 210 in this manner while holding the stop rod 250 and hence, the implant 100, stationary, causes the implant 100 to be delivered out of the hollow shaft 230 and into the subject.

Once cannula 210 is withdrawn from the tunnel, the surgeon can check the position of implant 100 inside the tunnel. The surgeon can confirm proper placement of implant 100 by palpation and inspection of the incision. After correct placement is confirmed, the surgeon or other medical professional should cover the insertion site with sterile gauze, apply pressure to the insertion site, and follow any other post-operative procedures that are required.

To remove implant 100, an incision is made transverse to the long axis of the upper arm adjacent to one end of the implant. The incision should be of a size adequate to allow the tips of a hemostat to enter the tunnel. The tips of the hemostat are inserted into the incision and positioned on opposite sides of implant 100 in a position to grasp the implant. Implant 100 is then grasped and carefully pulled out of the pocket. After implant 100 is removed, the surgeon or other medical professional should cover the insertion site with sterile gauze, apply pressure to the insertion site, and follow any other post-operative procedures that are required.

Many elements shown in the illustrated embodiments are ornamental elements. The appearance of each ornamental element is not dictated by any function that the feature may perform. Rather, the appearance of each ornamental feature is selected based on aesthetic considerations. These ornamental elements may have a wide variety of shapes, colors, dimensions and surface textures that are selected individually, or in combination, to achieve a desired product appearance. For example, the shape, contours and relative dimensions of flanges 221 on insertion instrument 200 need not be as shown in FIGS. 8-16, which show the flanges as crescent-shaped elements. Flanges 221 may be larger or smaller, and/or have other shapes such as triangular or rectangular shapes, without changing any functional aspects of insertion instrument 200. Other ornamental aspects of insertion instrument 200 include, but are not limited to, the circular perimeter of handle portion 224 (which can be any shape), the common border between the circular perimeter of the handle portion and the perimeter of each flange, the rounded transitions between the handle portion and front hub 223, the off-centered axial position of the handle portion with respect to the front hub 223, and the differences in length and diameter among the various parts of the hub and stop rod. The tunneling tool 300 also has many ornamental features, including but not limited to the compound curvatures on superior surface 366 of gripping portion 358, the compound curvatures on inferior surface 368 of the gripping portion, the hourglass shaped profile of the gripping portion (FIG. 23), the curved sides and rounded corners of overmolded grip 372 (FIGS. 19 and 20), the U-shape of base section 356 (FIGS. 21-23), and the contrasting surface texture between overmolded grip 372 and gripping portion 358. These ornamental aspects of the embodiments, which are only some of the ornamental aspects shown on the embodiments, do not influence the utilitarian aspects of the instruments or the functional purposes of any parts, and therefore may be replaced by an infinite number of other ornamental designs.

EXAMPLES

Embodiments of the present invention may be further understood by reference to the Examples provided below.

Example 1

Tizanidine Free Base+Variation of Sorption Enhancer

The follow general procedure was followed for the manufacture of an implant. Tubing was received in continuous length rolls and was cut to an appropriate starting length using a single-edged razor blade (or suitably sized scalpel). One end of each tubing section was thermally sealed imparting a semi-spherical closure on the tip of the tubing section.

Drug substance and a sorption enhancer were premixed in a Turbula blender. Stearic acid as a lubricant was added and the mixture again mixed in a Turbula blender.

The drug blend was compacted using a single punch tablet press. Drug pellets were manually placed inside each sealed section of tubing. The open section of each pellet-containing tubing section was then sealed into a semi-spherical seal. Sterilization was accomplished by gamma irradiation of the implants.

The implant dimensions were a total length of the implant of about 40 mm, an OD of 4.0 mm, an ID of 3.6 mm and a wall thickness of 0.2 mm. Nine pellets of a drug blend with various concentrations of tizanidine free base as the active pharmaceutical ingredient ("API") and croscarmellose, with the remainder being 2% stearic acid as lubricant, were placed into a polyurethane tubing (TECOFLEX® EG-80A). The API was varied to accommodate the increasing amounts of the sorption enhancer, with 405 mg API used in the implant containing 5% croscarmellose in the drug pellets, 385 mg API used in the implants containing 10% croscarmellose in the drug pellets, and 360 mg API used in the implants containing 15% croscarmellose in the drug pellets. The implants were sterilized by gamma irradiation and placed in an elution bath consisting of 100 mL PBS at 37° C. Weekly exchanges of the elution media were analyzed by HPLC for 27 weeks, and the results are shown in FIG. 4. At the lowest concentration of croscarmellose (5%), elution was about 1,200 µg/day at week 2 before slowly declining to about 900 µg/day at week 27, while the highest concentration of croscarmellose (15%) achieved an elution rate of about 1,400 µg/day at week 2 before slowly declining to about 1,250 µg/day at week 27, enabling the control of the drug release through the addition of various levels of sorption enhancers.

Example 2

PEBAX® Implants

The follow general procedure was followed for the manufacture of an implant. Tubing was received in continuous length rolls and was cut to an appropriate starting length using a single-edged razor blade (or suitably sized scalpel). One end of each tubing section was thermally sealed imparting a semi-spherical closure on the tip of the tubing section.

The API and a sorption enhancer, e.g. croscarmellose sodium, were premixed in a Turbula blender. Stearic acid as a lubricant is added and the mixture again mixed in a Turbula blender. The standard final drug blend was 88% API, 10% sorption enhancer, and 2% stearic acid powder.

The API blend was compacted using a single punch tablet press. Drug pellets were manually placed inside each sealed section of tubing. The open section of each pellet-containing tubing section was then sealed into a semi-spherical seal. Sterilization was accomplished by gamma irradiation of the implants.

A discrete solid dosage form was prepared as follows. The drug implants were manufactured using PEBAX® 2533 and PEBAX® 3533, as the tubing material and tizanidine free base as the API. The implant dimensions were a total length of the implant of about 50 mm, an OD of 4.0 mm, an ID of 3.6 mm and a wall thickness of 0.2 mm. A total of about 250 mg tizanidine free base were loaded into the implant with 10% croscarmellose and 2% stearic acid. The implant were sterilized by gamma irradiation and placed in an elution batch consisting of 200 mL 0.9% saline at 37° C. Weekly exchanges of the elution media were analyzed by HPLC for over 110 days, respectively. The graph is shown in FIG. 5. Release rates of tizanidine were between about 1,300 µg/day to about 1,700 µg/day.

Example 3

Tizanidine Hydrochloride

The follow general procedure was followed for the manufacture of an implant. Tubing was received in continuous length rolls and was cut to an appropriate starting length using a single-edged razor blade (or suitably sized scalpel). One end of each tubing section was thermally sealed imparting a semi-spherical closure on the tip of the tubing section.

The API and an sorption enhancer, e.g. croscarmellose sodium, were premixed in a Turbula blender. A lubricant is added and the mixture again mixed in a Turbula blender. The standard drug blend was 88% API, 10% sorption enhancer, and 2% lubricant.

The drug blend was compacted using a single punch tablet press. Drug pellets were manually placed inside each sealed section of tubing. The open section of each pellet-containing tubing section was then sealed into a semi-spherical seal. Sterilization was accomplished by gamma irradiation of the implants.

A discrete solid dosage form was prepared as follows. Various polyurethanes were used as the tubing material (i.e., TECOFLEX® EG-80A, TECOFLEX® EG-85A, TECOFLEX® EG-93A, TECOPHILIC® HP-60D-05, and TECOPHILIC® HP-60D-10 polyurethanes) and tizanidine hydrochloride as the API. The implant dimensions were a total length of the implant of about 50 mm, an OD of 4.0 mm, an ID of 3.6 mm and a wall thickness of 0.2 mm. A total of about 380 mg tizanidine hydrochloride were loaded into the implant with 10% croscarmellose and 2% stearic acid. The implants were sterilized by gamma irradiation and placed in an elution batch consisting of 200 mL PBS at 37° C. Weekly exchanges of the elution media were analyzed by HPLC over 5 weeks. The graph is shown in FIG. 6. The drug release from the implants was below 100 µg per day for all polyurethanes investigated.

Example 4

Tizanidine Free Base

The drug implants were manufactured as described in Example 3, except tizanidine free base was used as the API instead of tizanidine HCl. The implant dimensions were a total length of the implant of about 40 mm, an OD of 4.0 mm, an ID of 3.6 mm and a wall thickness of 0.2 mm. A total of about 250 mg tizanidine free base were loaded into the implants with 10% croscarmellose and 2% stearic acid. The implants were sterilized by gamma irradiation and placed in an elution batch consisting of 200 mL PBS at 37° C. Weekly exchanges of the elution media were analyzed by HPLC for up to 36 weeks. The graph is shown in FIG. 7. The drug release from the implants was about 10- to 15-fold higher with the tizanidine free base from the same polymers used with tizanidine HCl, even at lower API loading (i.e., 250 mg tizanidine free base vs. 380 mg tizanidine HCl), as can be seen in FIG. 7. Release rates varied from about 100 μg per day for TECOFLEX® EG-93A to about 900 μg per day for TECOFLEX® EG-80A.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A drug delivery composition comprising:
   a drug elution rate-controlling excipient comprising an elastomeric polymer defining a reservoir, and
   the reservoir contains at least one discrete solid dosage form comprising tizanidine free base,
   wherein the drug delivery composition is in an implantable dosage form, and wherein the elastomeric polymer comprises a polyether-based polyurethane.

2. The drug delivery composition according to claim 1, wherein the polyether-based polyurethane is an aliphatic polyether-based polyurethane comprising poly(tetramethylene oxide) and polymerized 4,4'-diisocyanato dicyclohexylmethane (H12MDI) and 1,4-butanediol.

3. The drug delivery composition according to claim 2, where the polyether-based polyurethane comprises a Shore hardness less than 87 A.

4. The drug delivery composition according to claim 1, wherein the at least one discrete solid dosage form is cylindrical.

5. The drug delivery composition according to claim 1, wherein the reservoir contains 5-10 discrete solid dosage forms.

6. The drug delivery composition according to claim 5, wherein the discrete solid dosage forms comprise about 100 mg to about 600 mg of the tizanidine free base.

7. The drug delivery composition according to claim 1, wherein the drug elution rate-controlling excipient is cylindrically shaped.

8. The drug delivery composition according to claim 1 wherein the at least one discrete solid dosage form comprises at least one sorption enhancer selected from the group consisting of croscarmellose sodium, sodium carboxymethyl starch, sodium starch glycolate, sodium acrylic acid derivatives, chondroitin sulfate, poly-glutamic acid, poly-aspartic acid, and combinations thereof.

9. A subcutaneous delivery system comprising:
   an elastomeric reservoir implant comprising at least one discrete solid dosage form surrounded by a polymeric rate-controlling excipient comprising a polyether-based polyurethane,
   the at least one discrete solid dosage form comprising tizanidine free base,
   wherein the subcutaneous delivery system provides for release of the tizanidine at an elution rate suitable to provide a therapeutically effective amount of the tizanidine to a subject at a zero order or pseudo-zero order rate for a period of time of at least one month.

10. A kit for subcutaneously placing a drug delivery composition comprising:
    a reservoir-based drug delivery composition comprising a polymeric rate-controlling excipient defining a reservoir containing at least one discrete solid dosage form comprising tizanidine free base; wherein said polymeric-rate controlling excipient comprises a polyether-based polyurethane and
    an implanter for inserting the reservoir-based drug delivery composition beneath the skin.

11. The drug delivery composition according to claim 1, wherein the at least one discrete solid dosage form further comprises croscarmellose.

12. The subcutaneous delivery system according to claim 9, wherein the at least one discrete solid dosage form further comprises croscarmellose.

13. The drug delivery composition according to claim 1, wherein the at least one discrete solid dosage form comprises:
    75-97 wt % tizanidine free base based on the total weight of the at least one discrete solid dosage form;
    1-25 wt % of at least one sorption enhancer based on the total weight of the at least one discrete solid dosage form; and
    0-5 wt % lubricant based on the total weight of the at least one discrete solid dosage form.

14. The subcutaneous delivery system according to claim 9, wherein the at least one discrete solid dosage form comprises:
    75-97 wt % tizanidine free base based on the total weight of the at least one discrete solid dosage form;
    1-25 wt % of at least one sorption enhancer based on the total weight of the at least one discrete solid dosage form; and
    0-5 wt % lubricant based on the total weight of the at least one discrete solid dosage form,
    wherein the subcutaneous delivery system provides for release of the tizanidine at a zero order or pseudo-zero order rate for a period of time of at least six months.

* * * * *